(12) United States Patent
Le et al.

(10) Patent No.: US 9,176,123 B2
(45) Date of Patent: Nov. 3, 2015

(54) BINDING-INDUCED HAIRPIN DETECTION SYSTEM

(75) Inventors: Xiaochun Le, Edmonton (CA); Hongquan Zhang, Edmonton (CA); Xing-Fang Li, Edmonton (CA)

(73) Assignee: THE GOVERNORS OF THE UNIVERSITY OF ALBERTA, Edmonton, Alberta (CA)

( * ) Notice: Subject to any disclaimer, the term of this patent is extended or adjusted under 35 U.S.C. 154(b) by 280 days.

(21) Appl. No.: 13/392,940

(22) PCT Filed: Aug. 30, 2010

(86) PCT No.: PCT/CA2010/001303
§ 371 (c)(1),
(2), (4) Date: Feb. 28, 2012

(87) PCT Pub. No.: WO2011/022820
PCT Pub. Date: Mar. 3, 2011

(65) Prior Publication Data
US 2012/0156678 A1   Jun. 21, 2012

Related U.S. Application Data

(60) Provisional application No. 61/238,368, filed on Aug. 31, 2009.

(51) Int. Cl.
*C12Q 1/68* (2006.01)
*C07H 21/00* (2006.01)
*G01N 33/53* (2006.01)
*G01N 33/542* (2006.01)

(52) U.S. Cl.
CPC .............. *G01N 33/53* (2013.01); *C12Q 1/6816* (2013.01); *G01N 33/542* (2013.01); *G01N 2458/10* (2013.01)

(58) Field of Classification Search
CPC ...... C12Q 1/68; C12Q 1/6813; C12Q 1/6816; C12Q 1/6844; C12Q 2525/205; C12Q 2525/30; C12Q 2525/301; C12N 15/11; C12N 15/115; C07H 21/00
USPC .................. 435/6.1, 91.2; 536/22.1
See application file for complete search history.

(56) References Cited

U.S. PATENT DOCUMENTS

| 4,683,195 | A | 7/1987 | Mullis et al. | |
|---|---|---|---|---|
| 4,683,202 | A | 7/1987 | Mullis | |
| 4,965,188 | A | 10/1990 | Mullis et al. | |
| 5,925,517 | A * | 7/1999 | Tyagi et al. | 435/6.1 |
| 7,306,904 | B2 | 12/2007 | Landegren et al. | |
| 2002/0192679 | A1* | 12/2002 | Chubinskaya et al. | 435/6 |
| 2005/0009050 | A1* | 1/2005 | Nadeau et al. | 435/6 |
| 2006/0040318 | A1* | 2/2006 | Melker et al. | 435/7.1 |
| 2007/0141610 | A1* | 6/2007 | Spier | 435/6 |
| 2007/0172873 | A1* | 7/2007 | Brenner et al. | 435/6 |
| 2007/0269825 | A1* | 11/2007 | Wang et al. | 435/6 |
| 2014/0170654 | A1* | 6/2014 | Landegren et al. | 435/6.11 |

FOREIGN PATENT DOCUMENTS

| WO | WO-9937806 A2 | 7/1999 |
|---|---|---|
| WO | WO-2007044903 A2 | 4/2007 |
| WO | WO-2011063388 A2 | 5/2011 |

OTHER PUBLICATIONS

Di Giusto et al. Proximity extension of circular DNA aptamers with real-time protein detection. Nucleic Acids Research 33(6) : e64 : 7 pages (2005).*
Broude et al. Stem-loop oligonucleotides:a robust tool for molecular biology and biotechnology. Trends in Biotechnology 20 (6) : 249 (2002).*
Supplementary European Search Report dated May 7, 2013, issued in EP Application No. 10811062.8.
Bonnet, et al., "Kinetics of conformational fluctuations in DNA hairpin-loops", Proc. Natl. Acad. Sci. USA, Jul. 1998, vol. 95, pp. 8602-8606.
Bonnet, et al., "Thermodynamic basis of the enhanced specificity of structured DNA probes", Proc. Natl. Acad. Sci. USA, May 1999, vol. 96, pp. 6171-6176.
Diatchenko, et al., "Suppression subtractive hybridization: A method for generating differentially regulated or tissue-specific cDNA probes and libraries", Proc. Natl. Acad. Sci. USA, Jun. 1996, vol. 93, pp. 6025-6030.
Ellington, et al., "In vitro selection of RNA molecules that bind specific ligands", Nature, Aug. 30, 1990, vol. 346, pp. 818-822.
Fredriksson, et al., "Protein detection using proximity-dependent DNA ligation assays", Nature Biotechnology, May 2002, vol. 20, pp. 473-477.
Green, et al., "Inhibitory DNA Ligands to Platelet-Derived Growth Factor B-Chain", Biochemistry, 1996, vol. 35, pp. 14413-14424.
Pearson, et al., "Trinucleotide repeat DNA Structures: dynamic mutations from dynamic DNA", Current Opinion in Structural Biology, 1998, vol. 8, pp. 321-330.
Sokol, et al., "Real time detection of DNA-RNA hybridization in living cells", Proc. Natl. Acad. Sci. USA, Sep. 1998, vol. 95, pp. 11538-11543.

(Continued)

*Primary Examiner* — Ethan C Whisenant
(74) *Attorney, Agent, or Firm* — Drinker Biddle & Reath LLP

(57) ABSTRACT

This application relates to a binding-induced hairpin detection system comprising: a. a first probe comprising a targeting molecule and an oligonucleotide that has a free end and an end attached to the targeting molecule; and b. a second probe comprising a targeting molecule and an oligonucleotide that has an end attached to the targeting molecule and a free end comprising a nucleotide sequence that is complementary to a nucleotide sequence at or near the free end of the oligonucleotide of the first probe; wherein upon binding of the targeting molecule to a target molecule, the free end of the oligonucleotide of the second probe hybridizes at or near the free end of the oligonucleotide of the first probe forming a hairpin stem, the non-hybridized portions of the first and second probes together with the target molecule bound thereto forming a hairpin loop, thereby providing a binding-induced hairpin.

15 Claims, 15 Drawing Sheets

(56) References Cited

OTHER PUBLICATIONS

Schallmeiner, et al., "Sensitive protein detection via triple-binder proximity ligation assays", Nature Methods, Feb. 2007, vol. 4, No. 2, pp. 135-137.

Tuerk, et al., "Systematic Evolution of Ligands by Exponential Enrichment: RNA Ligands to Bacteriophage T4 DNA Polymerase", Science, Aug. 3, 1990, vol. 249, pp. 505-510.

Tyagi, et al., "Molecular Beacons: Probes that Fluoresce upon Hybridization", Nature Biotechnology, Mar. 1996, vol. 14, pp. 303-308.

Tyagi, et al., "Multicolor molecular beacons for allele discrimination", Nature Biotechnology, Jan. 1998, vol. 16, pp. 49-53.

Tyagi, et al., "Wavelength-shifting molecular beacons", Nature Biotechnology, Nov. 2000, vol. 18, pp. 1191-1196.

Varani, Gabriele, "Exceptionally Stable Nucleic Acid Hairpins", Annu. Rev. Biophys. Biomol Struct., 1995, vol. 24, pp. 379-404.

Whitcombe, et al., "Detection of PCR products using self-probing amplicons and fluorescence", Nature Biotechnology, Aug. 1999, vol. 17, pp. 804-807.

Written Opinion of the International Searching Authority mailed Nov. 26, 2010 issued in PCT Application No. PCT/CA2010/001303 filed Aug. 30, 2010.

International Search Report mailed Nov. 26, 2010 isssued in PCT Application No. PCT/CA2010/001303 filed Aug. 30, 2010.

\* cited by examiner

SEQUENCE LISTING

<160> NUMBER OF SEQ ID NOS: 19

<210> SEQ ID NO 1
<211> LENGTH: 55
<212> TYPE: DNA
<213> ORGANISM: Artificial Sequence
<220> FEATURE:
<223> OTHER INFORMATION: aptamer

<400> SEQUENCE: 1
tttttttttt tactcagggc actgcaagca attgtggtcc caatgggctg agtat        55

<210> SEQ ID NO 2
<211> LENGTH: 58
<212> TYPE: DNA
<213> ORGANISM: Artificial Sequence
<220> FEATURE:
<223> OTHER INFORMATION: oligonucleotide

<400> SEQUENCE: 2
actgtgtctc gtcgttggtg ttttgttttg ttttaggctg gtcgctttgt tttgcgac     58

<210> SEQ ID NO 3
<211> LENGTH: 47
<212> TYPE: DNA
<213> ORGANISM: Artificial Sequence
<220> FEATURE:
<223> OTHER INFORMATION: oligonucleotide

<400> SEQUENCE: 3
cagccctttg tttgttttgt ttttttgat ggagcaggtg tcagatc                  47

<210> SEQ ID NO 4
<211> LENGTH: 48
<212> TYPE: DNA
<213> ORGANISM: Artificial Sequence
<220> FEATURE:
<223> OTHER INFORMATION: oligonucleotide

<400> SEQUENCE: 4
cagccttttt gtttgtttg tttttttga tggagcaggt gtcagatc                  48

<210> SEQ ID NO 5
<211> LENGTH: 49
<212> TYPE: DNA
<213> ORGANISM: Artificial Sequence

```
<220> FEATURE:
<223> OTHER INFORMATION: oligonucleotide

<400> SEQUENCE: 5
cagcctattt tgtttgtttt gttttttttg atggagcagg tgtcagatc          49

<210> SEQ ID NO 6
<211> LENGTH: 50
<212> TYPE: DNA
<213> ORGANISM: Artificial Sequence
<220> FEATURE:
<223> OTHER INFORMATION: oligonucleotide

<400> SEQUENCE: 6
cagcctaatt ttgtttgttt tgtttttttt gatggagcag gtgtcagatc          50

<210> SEQ ID NO 7
<211> LENGTH: 14
<212> TYPE: DNA
<213> ORGANISM: Artificial Sequence
<220> FEATURE:
<223> OTHER INFORMATION: oligonucleotide

<400> SEQUENCE: 7
tttgcctaaa attt          14

<210> SEQ ID NO 8
<211> LENGTH: 15
<212> TYPE: DNA
<213> ORGANISM: Artificial Sequence
<220> FEATURE:
<223> OTHER INFORMATION: oligonucleotide

<400> SEQUENCE: 8
tttgcctaaa acttt          15

<210> SEQ ID NO 9
<211> LENGTH: 16
<212> TYPE: DNA
<213> ORGANISM: Artificial Sequence
<220> FEATURE:
<223> OTHER INFORMATION: oligonucleotide

<400> SEQUENCE: 9
tttgcctaaa acattt          16

<210> SEQ ID NO 10
<211> LENGTH: 17
<212> TYPE: DNA
<213> ORGANISM: Artificial Sequence
<220> FEATURE:
<223> OTHER INFORMATION: oligonucleotide

<400> SEQUENCE: 10
tttgcctaaa acaattt          17

<210> SEQ ID NO 11
<211> LENGTH: 18
<212> TYPE: DNA
<213> ORGANISM: Artificial Sequence
<220> FEATURE:
<223> OTHER INFORMATION: oligonucleotide

<400> SEQUENCE: 11
tttgcctaaa acaaattt          18
```

```
<210> SEQ ID NO 12
<211> LENGTH: 14
<212> TYPE: DNA
<213> ORGANISM: Artificial Sequence
<220> FEATURE:
<223> OTHER INFORMATION: oligonucleotide

<400> SEQUENCE: 12
tttaaaggct gttt                                                       14

<210> SEQ ID NO 13
<211> LENGTH: 15
<212> TYPE: DNA
<213> ORGANISM: Artificial Sequence
<220> FEATURE:
<223> OTHER INFORMATION: oligonucleotide

<400> SEQUENCE: 13
tttaaaaggc tgttt                                                      15

<210> SEQ ID NO 14
<211> LENGTH: 16
<212> TYPE: DNA
<213> ORGANISM: Artificial Sequence
<220> FEATURE:
<223> OTHER INFORMATION: oligonucleotide

<400> SEQUENCE: 14
tttaaaaagg ctgttt                                                     16

<210> SEQ ID NO 15
<211> LENGTH: 17
<212> TYPE: DNA
<213> ORGANISM: Artificial Sequence
<220> FEATURE:
<223> OTHER INFORMATION: oligonucleotide

<400> SEQUENCE: 15
tttcaaaaag gctgttt                                                    17

<210> SEQ ID NO 16
<211> LENGTH: 15
<212> TYPE: DNA
<213> ORGANISM: Artificial Sequence
<220> FEATURE:
<223> OTHER INFORMATION: oligonucleotide

<400> SEQUENCE: 16
tttaataggc tgttt                                                      15

<210> SEQ ID NO 17
<211> LENGTH: 16
<212> TYPE: DNA
<213> ORGANISM: Artificial Sequence
<220> FEATURE:
<223> OTHER INFORMATION: oligonucleotide

<400> SEQUENCE: 17
tttaaatagg ctgttt                                                     16

<210> SEQ ID NO 18
<211> LENGTH: 17
<212> TYPE: DNA
<213> ORGANISM: Artificial Sequence
<220> FEATURE:
<223> OTHER INFORMATION: oligonucleotide
```

```
<400> SEQUENCE: 18
tttaaaatag gctgttt                                                    17

<210> SEQ ID NO 19
<211> LENGTH: 18
<212> TYPE: DNA
<213> ORGANISM: Artificial Sequence
<220> FEATURE:
<223> OTHER INFORMATION: oligonucleotide

<400> SEQUENCE: 19
tttcaaaata ggctgttt                                                   18
```

BINDING-INDUCED HAIRPIN DETECTION SYSTEM

CROSS-REFERENCE TO RELATED APPLICATIONS

This application is a National Stage of International Application No. PCT/CA2010/001303 filed Aug. 30, 2010, and claims the benefit of U.S. Provisional Patent Application No. 61/238,368, filed Aug. 31, 2009, which is incorporated herein by reference.

FIELD OF THE INVENTION

The present invention relates to a detection system that forms a binding-induced hairpin when bound to a target molecule, uses thereof and methods of detecting a target molecule in a sample.

BACKGROUND

Diverse approaches are available to detect the presence of molecules including, for example, ELISA, PCR and mass spectrometry. Landegren et al (U.S. Pat. No. 7,306,904) describe the detection of analytes in solution using proximity probes. These probes comprise a binding moiety and a nucleic acid molecule. The nucleic acid molecule of one proximity probe may interact with that of another when in close proximity, i.e. when bound to an analyte. The interacting nucleic acid molecules may be amplified to detect the presence of the analyte. However, high background is a common problem that limits the detection of target present at trace levels. For example, in the proximity ligation assay used by Landegren et al, the authors had to use very low concentrations of probes in order to keep the background low. Too low a concentration of the probes is not suitable for binding of the probes to a target molecule, since that would result in low sensitivity for the detection of the target molecules. However, increasing the concentration of the probes results in high background, which is problematic. Therefore, there is a trade-off, and Landegren et al does not differentiate target specific proximity ligation from non-target specific proximity ligation.

Thus there remains a need for a detection system that minimizes background and that forms a stable complex only when bound to a target molecule and wherein the stable complex may be specifically detected.

SUMMARY OF THE INVENTION

Accordingly, the present invention relates to a detection system in which a binding-induced hairpin is formed only upon binding to a target molecule. This system discriminates between a hairpin structure formed by the binding of a first and a second probe to a target molecule from unbound probes, i.e. background. When there is no target molecule the first and second probes may hybridize, but that hybridization is not stable (low Tm) at room temperature. Only in the presence of a target molecule is the binding-induced hairpin formed. The formation of this hairpin increases the stability of the hybridization, producing a stable, amplifiable hairpin structure.

Thus, in one aspect, the invention relates to a binding-induced hairpin detection system comprising: a. a first probe comprising a targeting molecule and an oligonucleotide that has a free end and an end attached to the targeting molecule; and b. a second probe comprising a targeting molecule and an oligonucleotide that has an end attached to the targeting molecule and a free end comprising a nucleotide sequence that is complementary to a nucleotide sequence at or near the free end of the oligonucleotide of the first probe; wherein upon binding of the targeting molecule to a target molecule, the free end of the oligonucleotide of the second probe hybridizes at or near the free end of the oligonucleotide of the first probe forming a hairpin stem, the non-hybridized portions of the first and second probes together with the target molecule bound thereto forming a hairpin loop, thereby providing a binding-induced hairpin.

In another aspect, the invention relates to a method of detecting a target molecule in a sample, the method comprising: a. providing the sample; b. incubating the sample with i. a first probe comprising a targeting molecule and an oligonucleotide that has a free end and an end attached to the targeting molecule; and ii. a second probe comprising a targeting molecule and an oligonucleotide that has an end attached to the targeting molecule and a free end comprising a nucleotide sequence that is complementary to a nucleotide sequence at or near the free end of the oligonucleotide of the first probe; c. contacting the sample with the first probe and the second probe, wherein upon binding of the targeting molecule to a target molecule, the free end of the oligonucleotide of the second probe hybridizes at or near the free end of the oligonucleotide of the first probe forming a hairpin stem, the non-hybridized portions of the first and second probes together with the target molecule bound thereto forming a hairpin loop, thereby providing a binding-induced hairpin; and d. detecting the binding-induced hairpin.

In another aspect, the invention relates to use of the detection system as described above for detecting a target molecule in a sample.

In a further aspect, the invention relates to use of a plurality of detection systems as described above, wherein each detection system of the plurality of detection systems has a distinct target specificity, for the detection of a plurality of distinct target molecules.

Advantages of the invention may include, without limitation, the production of low background and high sensitivity in the detection of a target molecule; the possible application of blocking oligonucleotides that further decreases target-independent hybridization and improves sensitivity of detected target molecules; the simplicity, ease of design and control, and theoretical predictability of the components of the detection system; and the favourable kinetics of the formation of a binding-induced hairpin.

Other aspects, advantages and features of the present invention will become apparent to those of ordinary skill in the art upon review of the following description of specific embodiments of the invention in conjunction with the accompanying figures.

DETAILED DESCRIPTION

Figure 1:
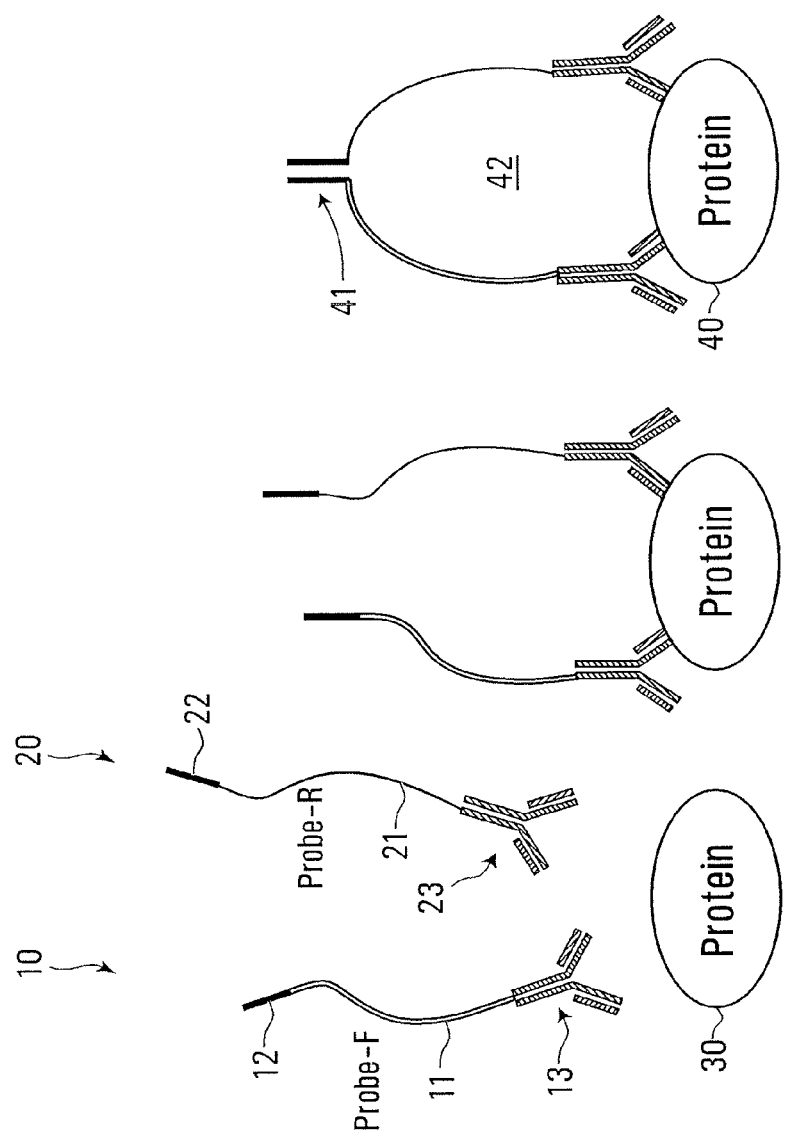
FIG. 1. One embodiment of the binding-induced hairpin detection system. (A) First and second probes are used to bind to a target molecule. (B) In the presence of target molecules, a first probe and a second probe bind to a single target molecule (or to two or more associated molecules), placing the two probes in proximity. (C) The free end of the first and second probes hybridize to form a hairpin stem, thereby forming a binding-induced hairpin structure. The nonhybridized portions of the first and second probes, together with the targeting molecules, and the target molecule (or the two or more associated molecules) bound thereto, form the hairpin loop of the binding-induced hairpin.

Hairpin structures are of great interest due to their stability and target specificity. Typically, a hairpin may result from the intramolecular base pairing that occurs in a single-stranded nucleic acid molecule, such as DNA or RNA. Specifically, a hairpin may occur when two regions of the same molecule, e.g. a palindromic nucleotide sequence, base-pair to form a double helix (stem) that ends in an unpaired loop (loop).

Nucleic acid molecules comprising hairpin structures may be found in cells, where they may play an important regulatory role in gene expression and cellular metabolism (1, 2). In addition, DNA hairpins may have advantages as hybridization probes. Thermodynamic studies have demonstrated that DNA hairpin probes show significantly higher specificity than the corresponding linear probes (3, 4). DNA hairpin probes can generally distinguish targets that are different from one another by as little as a single nucleotide substitution. The enhanced specificity is due to their constrained secondary structures. An example of a DNA hairpin probe is a molecular beacon. A molecular beacon is a hairpin-shaped DNA molecule possessing a fluorophore at the end of one stem arm and a quencher at the end of the other arm (5-7). In the absence of targets, the stem places the fluorophore and the quencher in close proximity so that the fluorophore is unable to fluoresce. When they encounter a target nucleic acid molecule, hybridization of the molecular beacon to its target detaches the hybrid formed by the arm sequences, thereby causing the fluorophore and quencher to separate. As a result, the fluorescence of the fluorophore is restored, which may be used as a signal for the detection of the target nucleic acid molecule.

DNA hairpins have been widely applied to detection, amplification, and manipulation of nucleic acids (8-10). However, application of hairpin structures for the detection of other macromolecules has been limited. Current techniques involving hairpin structures, such as molecular beacons, usually start with probes possessing hairpin structures but which undergo a conformational change that abolishes the hairpin structure upon hybridization to a target nucleic acid molecule. However, the present invention makes use of the unique properties of hairpin structures in a detection system in which a novel hairpin structure is formed upon binding to a target molecule.

Detection System

The present invention is based on the formation of a binding-induced hairpin, in which the novel hairpin structure forms once a detection system of the invention binds to a target molecule. This binding-induced hairpin is a stable structure that may be detected with high specificity.

The detection system of the invention comprises a first probe and a second probe. The first probe comprises a targeting molecule and an oligonucleotide that has a free end and an end attached to the targeting molecule. The second probe comprises a targeting molecule and an oligonucleotide that has an end attached to the targeting molecule and a free end that is complementary to nucleotides at or near the free end of the oligonucleotide of the first probe. When the first and second are brought into proximity, for example by binding to the same target molecule, complementary nucleotides at or near the free ends of the oligonucleotides of the first and second probes may hybridize forming a binding-induced hairpin. The specific sequence of nucleotides of each oligonucleotide that hybridize, e.g. base-pair, form the stem of the binding-induce hairpin. The nonhybridized portions of the each oligonucleotide of the first and second probes together with the target molecule bound thereto, form the hairpin loop of the binding-induced hairpin.

As used herein, "binding-induced hairpin" refers to a hairpin structure that is formed only when the first and second probes of the detection system bind to a target molecule, thus permitting the free ends of the bound probes to hybridize to form the hairpin stem, while the remaining portions of the probe together with the bound target molecule form the hairpin loop.

As used herein, "hybridize" or "hybridization" refers to the association of two complementary single-stranded nucleic acid molecules to form a hybrid double-stranded nucleic acid molecule. Hybridization may refer to the association of two complementary single-stranded nucleic acid molecules over its entire length; or may be limited to portions of the two single-stranded nucleic acid molecules that are complementary. In the context of the invention, the terms "hybridize" or "hybridization" may also refer to the formation of the stem of a hairpin structure due to the association of two single-stranded nucleic acid molecules at specific portions that are complementary. Complementary portions of two single-stranded nucleic acid molecules may comprise a sequence of at least 2, at least 3, at least 4, at least 5, at least 6, at least 7, at least 8, at least 9, at least 10, at least 11, at least 12, at least 13, at least 14, at least 15, at least 16 or more complementary nucleotides. Typically, the stem sequence should have at least 3 base-pairs; however the number suitable base-pairs may vary depending on the design of the probe and in consideration of the target molecule at issue.

In one embodiment, complementary portions of two single-stranded nucleic acid molecules may contain at most 1, at most 2, or at most 3 pairs of non-complementary (mismatch) nucleotides. In this regard, the degree of mismatch that is acceptable in the context of the invention may be determined in consideration of the differences in melting temperatures between hybridized probes in a binding-induced hairpin and hybridized free probes (i.e. not bound to a target molecule). There are two requirements that need consideration. First, the melting temperature of the hybridize probes in a binding-induced hairpin should be at least 2 degrees higher than experimental temperature. In other words, stem sequences containing any mismatch may still form a stable hairpin structure upon binding of probes to a target molecule. Second, based on the first requirement, the difference of melting temperatures between the hybridized probes in the binding-induced hairpin and the hybridized free probes should be as large as possible in order to achieve high sensitivity and low background. The melting temperature of hybridized probes in a binding-induced hairpin and that of hybridized free probes may be estimated by available software, such as IDT's Oligo Analyzer, and Zuker DNA folding program.

A detection system of the invention may be designed having regard to interaction between and/or among the components of the detection system. For example, consideration may be given to the interaction between the first and second probes; the interaction between the oligonucleotide and the targeting molecule; and the interaction between the targeting molecule and the target molecule. In this regard, the skilled person would appreciate that available software may be used to assist in probe design. Exemplary software suitable for probe design include, without limitation, IDT's Oligo Analyzer and Zuker DNA folding program.

An oligonucleotide of the first probe may hybridize to that of the second probe once the first and second probes are in proximity, e.g. by binding to the same target molecule or two distinct but associated molecules. However, background hybridization may occur, i.e. in the absence of binding of the detection system to a target molecule. Conditions may be optimized to reduce background hybridization. For example, the nucleotides at or near the free end of the oligonucleotides that hybridize to each other to form the stem of the binding-induced hairpin may be targeted for optimization. In one instance, the length and composition of the nucleotide sequences at or near the free end of the oligonucleotides may be varied, for example, using standard techniques and following known molecular forces between nucleotides, to reduce background hybridization. In another instance, the temperature at which the binding reaction takes place may be adjusted to be biased against background hybridization.

Similarly, routine techniques may be employed to reduce background interactions (or any unintended or undesired interactions) between the oligonucleotide and the targeting molecule or the target molecule.

Conversely the skilled person would appreciate that similar approaches may be used to favour intended interactions, e.g. the formation of a binding-induced hairpin. This may involve, for example, a consideration of the size, shape and composition of the oligonucleotides, the targeting molecules and the target molecule.

Probes—Oligonucleotides

A detection system of the invention comprises a first probe and a second probe. The first probe and the second probe each comprises a targeting molecule and an oligonucleotide that has a free end and an end attached to the targeting molecule. A first probe may hybridize to a second probe due to the presence of complementary nucleotides at or near the free end of the oligonucleotides of each of said probes.

Oligonucleotides of the invention may comprise any size, shape and composition that is suitable for use in the context of the invention. In one embodiment, the size, shape and/or composition of the oligonucleotide of the first probe may differ from that of the second probe. In another embodiment, the size, shape and/or composition of the oligonucleotide of first and second probes may be substantially similar, with the exception of the portions of the oligonucleotides that hybridize to form the stem of the binding-induced hairpin.

Preferably, an oligonucleotide of the invention may comprise DNA, RNA, synthetic nucleotides, non-natural nucleotides, altered nucleotides, or combinations of one or more thereof. In one embodiment, an oligonucleotide of the invention may comprise locked nucleic acids and/or peptide nucleic acids. A detection system of the invention may comprise oligonucleotides of different compositions of matter. For example, the oligonucleotide of the first probe may comprise DNA, whereas the oligonucleotide of the second probe may comprise RNA.

As used herein, "nucleic acid", "nucleotide sequence" or "nucleic acid molecule" refers to a polymer of DNA and/or RNA which may be single or double stranded and optionally containing synthetic, non-natural or altered nucleotide bases capable of incorporation into DNA or RNA polymers. "Nucleic acids", "Nucleic acid sequences" or "Nucleic acid molecules" may encompass genes, cDNA, DNA and RNA encoded by a gene. Nucleic acids or nucleic acid sequences may comprise at least 3, at least 10, at least 100, at least 1000, at least 5000, or at least 10000 nucleotides or base pairs.

"Nucleic acids", "Nucleic acid sequences" or "Nucleic acid molecules" may be modified by any chemical and/or biological means known in the art including, but not limited to, reaction with any known chemicals such as alkylating agents, browning sugars, etc; conjugation to a linking group (e.g. PEG); methylation; oxidation; ionizing radiation; or the action of chemical carcinogens. Such nucleic acid modifications may occur during synthesis or processing or following treatment with chemical reagents known in the art.

Probes of the invention may be of any length provided that they allow the formation of a binding-induced hairpin structure once bound to a target molecule. In one embodiment, the oligonucleotide of the first probe and that of the second probe may comprise nucleotides and are sufficiently long, such that when the first and second probes bind to a target molecule, the free ends of the oligonucleotides may be able to hybridize to form the stem of the binding-induced hairpin. The skilled person may use the size of the target molecule and that of the targeting molecule to estimate a suitable size of the first and second probes. However, the length of the probes may not be so long as to affect the stability of the binding-induced hairpin structure. For example, an oligonucleotide of the first and/or second probe may comprise a sequence of at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 125, at least 150, at least 175, at least 200, at least 250, or more nucleotides. A preferred oligonucleotide may comprise a sequence of between about 50 and about 100 nucleotides. The oligonucleotides should be long enough such that when a first and a second probe binds to a single target molecule (or to two or more associated molecules), nucleotides at or near the end of the oligonucleotide of the first and second probes may hybridize.

In one embodiment, the free end of the oligonucleotide of the first probe may further comprise a hairpin. This is a pre-existing hairpin and thus is different from a binding-induced hairpin. In this regard, the loop of the hairpin at the free end of the oligonucleotide of the first probe may be of any length and composition that is suitable for use in the context of the invention. The skilled person would appreciate that the loop of pre-existing hairpin may be long enough to form the hairpin structure. For example, the loop of a pre-existing hairpin may comprise a sequence of at least 3, at least 4, at least 5, at least 6, at least 7, at least 8, at least 9, at least 10, at least 11, at least 12, at least 13, at least 14, at least 15, at least 16, or more nucleotides. In one embodiment, the hairpin loop is between about 4 and about 8 nucleotides in length. In another embodiment, the hairpin loop may have the well known sequence UUCG. In a further embodiment, the hairpin loop may have the sequence TTTGTTTTT, as described in SEQ ID NO: 2.

The stem of the pre-existing hairpin at the free end of the first probe may be of any length and composition that is suitable for use in the context of the invention. For example, the hairpin stem may comprise a sequence of at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20 or more paired nucleotides. In one embodiment, the stem of the hairpin at the free end of the first probe may comprise a sequence of between about 3 and about 13 paired nucleotides. In an embodiment of the invention, this stem may contain no mismatched nucleotides. In other embodiments, this stem may contain at most 1, at most 2, or at most 3 pairs of non-complementary (mismatch) nucleotides.

The skilled person would appreciate that the length and composition of the pre-existing hairpin may vary, but as long as it is stable under experimental temperature, it may be suitable for use in the context of the invention.

Nucleotides at the free end of the oligonucleotide of the second probe may hybridize to complementary nucleotides at or near the free end of the oligonucleotide of the first probe. In one embodiment of the invention, the free end of the oligonucleotide of the second probe may comprise a sequence of at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20 or more nucleotides that are complementary to a sequence of, respectively, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20 or more nucleotides at or near the free end of the oligonucleotide of the first probe.

The complementary nucleotides between the first and second probes may comprise a sequence of at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20 or more contiguous nucleotides. Alternatively, the sequence of complementary nucleotides between the first and second probes may contain at most 1, at most 2 or at most 3 mismatched nucleotides.

In embodiments of the invention, the oligonucleotide of the first probe may comprise, consist or consist essentially of the sequence depicted in SEQ ID NO: 2; and/or the oligonucleotide of the second probe may comprise, consist or consist essentially of any one of the sequences depicted in SEQ ID NOs: 3-6.

As used herein, "consist essentially of" or "consisting essentially of" means that the probes or the blocking agents may include, for example, nucleotide residues, including within the oligonucleotide sequence or at one or both ends of the oligonucleotide sequence, but that the additional residues do not materially affect the hybridization of the probes to each other; or the hybridization of the blocking agents to the probes.

The construction, purification and analysis of the probes may be achieved by methods known in the art.

With respect to construction, a skilled person can construct the first and second probes of the detection system based on known molecular techniques. In one embodiment, the probes may be synthesized chemically by methods known in the art. In other embodiments, the probes may be produced recombinantly or may be isolated from a source, e.g. an organism such as a bacteria, a virus, an animal, a human or a plant. If the first probe comprises a hairpin structure, it may be subject to suitable conditions to allow the hairpin structure to form.

Once produced, the probes may be purified with methods and techniques known in the art. Exemplary purification methods include, but are not limited to, affinity chromatography, size exclusion chromatography, Immobilized Metal Chelating Chromatography (IMAC), and agarose/acrylamide gel electrophoresis. One or more of these approaches may also be used to determine if the produced probe is of the intended size, shape, weight and/or composition. The composition of the produced probe may be verified by routine techniques, e.g. sequencing where the probe comprises nucleotides or amino acids; mass spectrometry; and single-stranded conformational polymorphism (sscp).

Targeting Molecule

A detection system of the invention comprises first and second probes, each comprising an oligonucleotide and a targeting molecule. A targeting molecule of the invention may be any molecule that may be used to bind to, or associate with, a target molecule. In embodiments of the invention, the targeting molecule may be, without limitation, an aptamer, a ligand, a receptor or an antibody.

As used herein, an "aptamer" may be a nucleic acid or a peptide molecule that binds to a specific molecular target. For example, in solution, a chain of nucleotides may form intramolecular interactions that fold the aptamer into a complex three-dimensional shape. The shape of that aptamer allows it to bind tightly against the surface of its target molecule. Because of the diversity of molecular shapes that exists for nucleotide and amino acid sequences, aptamers may be obtained for a wide array of molecular targets, including, but not limited to, enzymes, membrane proteins, viral proteins, cytokines, growth factors, and immunoglobulins.

An aptamer of the invention may be a nucleic acid molecule. Said aptamer may comprise DNA, RNA, synthetic nucleotides, non-natural nucleotides, altered nucleotides, or combinations of one or more thereof. The nucleic acid aptamer may be single-stranded or double-stranded. A nucleic acid aptamer may comprise a sequence of at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 125, at least 150, at least 175, at least 200, at least 250, at least 300, at least 350, at least 400, at least 500, or more nucleotides. A preferred nucleic acid aptamer may be a single stranded nucleic acid molecule and comprise a sequence of less than about 100 nucleotides.

An aptamer of the invention may be a peptide molecule. A peptide aptamer may comprise a sequence of at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 125, at least 150, at least 175, at least 200 or more amino acid residues. A preferred peptide aptamer may comprise a sequence of between about 15 to about 75 amino acid residues.

As used herein, the terms "peptide", "oligopeptide", "polypeptide" and "protein" may be used interchangeably and may encompasses any chain of naturally or non-naturally occurring amino acids (either D- or L-amino acids), regardless of length (e.g., at least 5, 6, 8, 10, 12, 14, 16, 18, 20, 25, 30, 40, 50, 100 or more amino acids) or post-translational modification (e.g., glycosylation or phosphorylation) or the presence of e.g. one or more non-amino acyl groups (for example, sugar, lipid, etc.) covalently linked to the peptide, and includes, for example, natural proteins, synthetic or recombinant polypeptides and peptides, hybrid molecules, peptoids, peptidomimetics, etc. Peptides may also be monomeric or multimeric. Peptide fragments may comprise a contiguous span of at least 5, at least 10, at least 25, at least 50, at least 100, at least 250, at least 500, at least 1000, at least 1500, or at least 2500 consecutive amino acids and may retain the desired activity of the full length peptide.

As used herein, a "ligand" may be any substance that is able to bind to and form a complex with a biomolecule. For example, a ligand may be a signal triggering molecule that binds to a site on a target molecule, by intermolecular forces such as ionic bonds, hydrogen bonds and Van der Waals forces. The association of the ligand to the biomolecule may be reversible or irreversible, e.g. by covalent bond. Ligands may include, for example, substrates, inhibitors (e.g. antagonists), activators (e.g. agonists), and neurotransmitters. A ligand may also be an oligonucleotide sequence, a lipid, a glycan, a drug, a virus, etc.

As used herein, a "receptor" may be any molecule, typically a protein molecule, to which another molecule, typically a signaling molecule, may bind. Typically, a molecule that binds to a receptor may be referred to as a "ligand," and may be a peptide (such as a neurotransmitter), a hormone, a pharmaceutical drug, or a toxin, and when such binding occurs, the receptor may undergo a conformational change which ordinarily initiates a cellular response. However, some ligands block receptors without inducing any response (e.g. antagonists). Ligands may also include agonists, i.e. a substance that binds to a receptor and triggers a response by the cell. An agonist often mimics the action of a naturally occurring substance.

As used herein, an "antibody" may include monoclonal antibodies (including full length monoclonal antibodies), polyclonal antibodies, multispecific antibodies (e.g., bispecific antibodies), single domain antibodies and antibody fragments. "Antibody fragments" comprise a portion of a full length antibody, generally the antigen binding or variable region thereof. Examples of antibody fragments include, but are not limited to, Fab, Fab', F(ab')2, and Fv fragments; diabodies; linear antibodies; single-chain antibody molecules; and multi-specific antibodies formed from antibody fragments. The term "antibody" may also include chimeric or humanized antibodies.

A targeting molecule of the invention may be prepared according to standard techniques know to the skilled person. For example, the targeting molecule may be produced synthetically, recombinantly or may be isolated from a source. In one embodiment, the source may be a biological source, preferably from a microorganism (e.g. a bacteria or a virus), an animal (e.g. a mouse, a rat, a rabbit, a goat, or a human), or a plant.

A detection system of the invention may comprise one or more types of targeting molecules. In one embodiment first and second probes may comprise the same type of targeting molecule. For instance, the targeting molecule of the first probe and that of the second probe may both be antibodies. In another embodiment, the first probe and the second probe may comprise distinct types of targeting molecules. For instance, the targeting molecule of the first probe may be an antibody; whereas the targeting molecule of the second probe may be an aptamer, or any molecule other than an antibody.

A detection system of the invention may comprise targeting molecules that bind to one or more target molecules. In one embodiment, the targeting molecule of the first probe and that of the second probe may bind to the same target molecule. In this instance, the targeting molecule of the first and second probes may bind to adjacent sites or distal sites on the same target molecule.

In another embodiment, the targeting molecule of the first probe and that of the second probe may bind to separate target molecules. In one instance, the targeting molecule of the first probe and that of the second probe may bind to separate but identical target molecules, provided the separate but identical target molecules may interact and/or associate with each other (e.g. homodimers or protein aggregates). In another instance, targeting molecule of the first probe and that of the second probe may bind to separate and distinct target molecules, provided the separate and distinct target molecules may interact and/or associate with each other (e.g. heterodimers, molecules of one of the following exemplary relationships: substrate/enzyme; and ligand/receptor). In a further instance, the targeting molecule of the first probe and that of the second probe may bind to separate and distinct target molecules, where the separate and distinct target molecules do not directly interact and/or associate with each other. In this regard, the separate and distinct target molecules may interact via one or more intermediate molecule.

Various ligands could be employed to create the probes, depending on the target and the availability of ligands. In order to achieve better sensitivity, ligands with higher affinity are preferred, because these ligands allow a larger portion of the target molecules involved into the hairpin structure.

Linker

A detection system of the invention comprises a first probe and a second probe, each of which comprises a targeting molecule attached to an end of an oligonucleotide. The oligonucleotide may be attached directly or indirectly to a targeting molecule. In one embodiment, an oligonucleotide is attached directly to a targeting molecule, e.g. by a chemical bond. In another embodiment, an oligonucleotide is attached indirectly to a targeting molecule via a linker. As used herein, a "linker" may also refer, without limitation, to linking of an oligonucleotide to a targeting molecule by chemical cross-linking.

A linker of the invention may refer to any molecule or a series of associated molecules that are used to attach an oligonucleotide to a targeting molecule of a probe; provided that the linker does not interfere with the hybridization of the first and second probes or with the binding of the targeting molecule to a target molecule. As used herein, "associate" or "associated" means that the two or more molecules can, reversible or irreversible, bind, interact, attach or form bonds to one another.

For example, a linker may be a peptide. A typical peptide linker may comprise a sequence of at least 1, at least 2, at least 3, at least 4, at least 5, at least 6, at least 7, at least 8, at least 9, at least 10, at least 11, at least 12 and preferably less than 200, less than 150, less than 100, less than 90, less than 80, less than 70, less than 60, less than 50, less than 40, less than 30 or less than 20 amino acid residues.

In another example, a linker may comprise a spacer, e.g. polyethylene glycol (PEG). In this regard, PEG may be cross-linked to the oligonucleotide and to a targeting molecule of a probe.

In further example, an oligonucleotide and a targeting molecule may be linked by a binding pair. An exemplary binding pair includes without limitation, biotin and streptavidin. In this regard, an oligonucleotide may be linked to or associated with biotin and a targeting molecule may be linked to or associated with streptavidin; or vice versa. Any binding pair may be suitable for use in the context of the invention, provided that neither component of the binding pair interferes with the interaction between the targeting molecule and the target molecule; unless the targeting and target molecules comprise the binding pair.

The skilled person would appreciate that the size, shape and composition of the linker may be varied as necessary. For example, the length of a linker may be tailored to facilitate the formation of a binding-induced hairpin.

Target Molecule

A target molecule of the invention may be any molecule that binds to a targeting molecule. In one embodiment, the target molecule is a single molecule. In another embodiment, the target molecule may be a complex of two or more molecules that can associate with each other. Preferably, the target molecule may be recognized by two targeting molecules.

As used herein, a "target molecule" may include, but is not limited to, lipids, polysaccharides, glycans, proteins, oligonucleotide sequences, cells or fragments thereof, and drugs. A preferred group of target molecules are proteins, which include without limitation, enzymes, toxins, cell receptors, ligands, viral or bacterial proteins or antigens, signal transducing agents, cytokines, antibodies, prions and growth factors (e.g. PDGF). The target molecule may include natural and non-naturally occurring modifications thereof. For example, modifications of the target molecule may include in vivo and/or in vitro chemical derivatization of polypeptides, e.g., acetylation, carboxylation, phosphorylation, or glycosylation; such modifications may occur during polypeptide synthesis or processing or following treatment with isolated modifying enzymes.

A target molecule of the invention may be any molecule used in the diagnosis of a person having or at risk of developing a disease. For example, a target molecule may be a molecule that is marker of, or is associated with, a disease of humans, animals or plants. A disease in humans may include without limitation, a disease that is localized, e.g. an organ (such as heart, lung, kidney, liver, skin, bone) or that is systemic, e.g. in blood, lymph nodes.

Preferred target molecules used in the diagnosis of a person having or is at risk of developing a disease may include, but are not limited to, antigens. As used herein, the term "antigen" refers to any substance that elicits an immune response, either antibody or cellular, in animals. For example, the antigen may be a proteinaceous substance. Antigens may include, without limitation, those derived from cancer, autoimmune diseases and infectious disease agents such as viruses and bacteria.

Exemplary infectious viral and/or bacterial antigens include, but are not limited to, the HA (hemagglutinin) protein of AIV (Avian Influenza Virus); the HN (hemagglutinin/neuraminidase) protein of avian Newcastle Disease Virus; VP2, of infectious bursa disease virus (IBDV); an enzyme ADP ribosyl transferase (LT-A subunit of heat labile toxin of *E. coli*); a bacterial toxin LT of *E. coli*; and proteins derived from human viruses including, but not limited to, poliovirus, human rhinovirus, hepatitis A virus, human immunodeficiency virus, human influenza, human papillomavirus, herpes simplex virus, picornaviruses such as foot-and-mouth disease virus, Dengue and West Nile viruses and respiratory syncytial virus.

Exemplary cancer disease associated and/or specific antigens include, but are not limited to, carcinoembryonic antigen (CEA), prostate specific antigen (PSA), prostate-specific membrane antigen (PSM), melanoma antigens (MAGE, BAGE, GAGE), mucins, such as MUC-1; HER2-neu and HPV.

Exemplary antigens associated with autoimmune disease include, but are not limited to, transglutaminase in celiac disease, muscle actin in autoimmune hepatitis, *Bullous Pemphigoid* antigen 1 and 2, basement membrane collagen Type IV protein in Goodpasture's syndrome, ganglioside in Guillain-Barre syndrome, myelin basic protein in multiple sclerosis, desmogein 3 in *Pemphigus vulgaris*, p62/sp100/mitochondrial (M2) in primary biliary cirrhosis, rheumatoid factor in rheumatoid arthritis, and topoisomerase in Scleroderma In other embodiments, the target molecule may be a molecule that is marker of, or is associated with, a cell, a tissue, or an organ. For example, the target molecule may be constitutively present in a cell, a tissue or an organ. In another example, the target molecule may be present intermittently. In this regard, the intermittent expression of a target molecule may be due to intracellular (e.g. replication, mutation), extracellular (e.g. viral or bacterial infection) and/or developmental factors (e.g. maturation of lymphocytes).

Formation of a Binding-Induced Hairpin

A detection system of the present invention may form a binding-induced hairpin upon binding to a target molecule (or to two or more distinct but associated molecules). A binding-induced hairpin may be formed by way of one of the following exemplary models.

In one embodiment, a detection system of the invention may be used to detect a target molecule, forming a binding-induced hairpin as follows: see FIG. 1: (A). A first probe 10 and a second probe 20 are used to bind to target molecule 30. Target molecule 30 may be a single molecule or two or more associated molecules. In the absence of targets, the first and second probes are typically present separately. The length of stem sequences may be short enough so that the free probes typically do not hybridize together. Targeting molecules 13 and 23 are merely depicted as antibodies, but may be any targeting molecule as described herein. (B) In the presence of target molecules, a first probe and a second probe bind to a single target molecule (or to two or more associated molecules), placing the two probes in proximity. (C) As a result, nucleotides at the free end 22 of the oligonucleotide of the second probe 20 may hybridize to complementary nucleotides at the free end 12 of the oligonucleotide of the first probe 10, forming a hairpin stem 41, thereby forming a binding-induced hairpin structure 40. Because this hairpin structure is induced upon the binding of probes to the target molecule, it is termed as binding-induced hairpin. Unlike a traditional nucleotide hairpin, the binding-induced hairpin is a complex structure. Indeed, the nonhybridized portions of the probes 11 and 21, together with the targeting molecules 13 and 23, and the target molecule (or the two or more associated molecules) bound thereto 30, form the hairpin loop 42 of the binding-induced hairpin.

Figure 2:
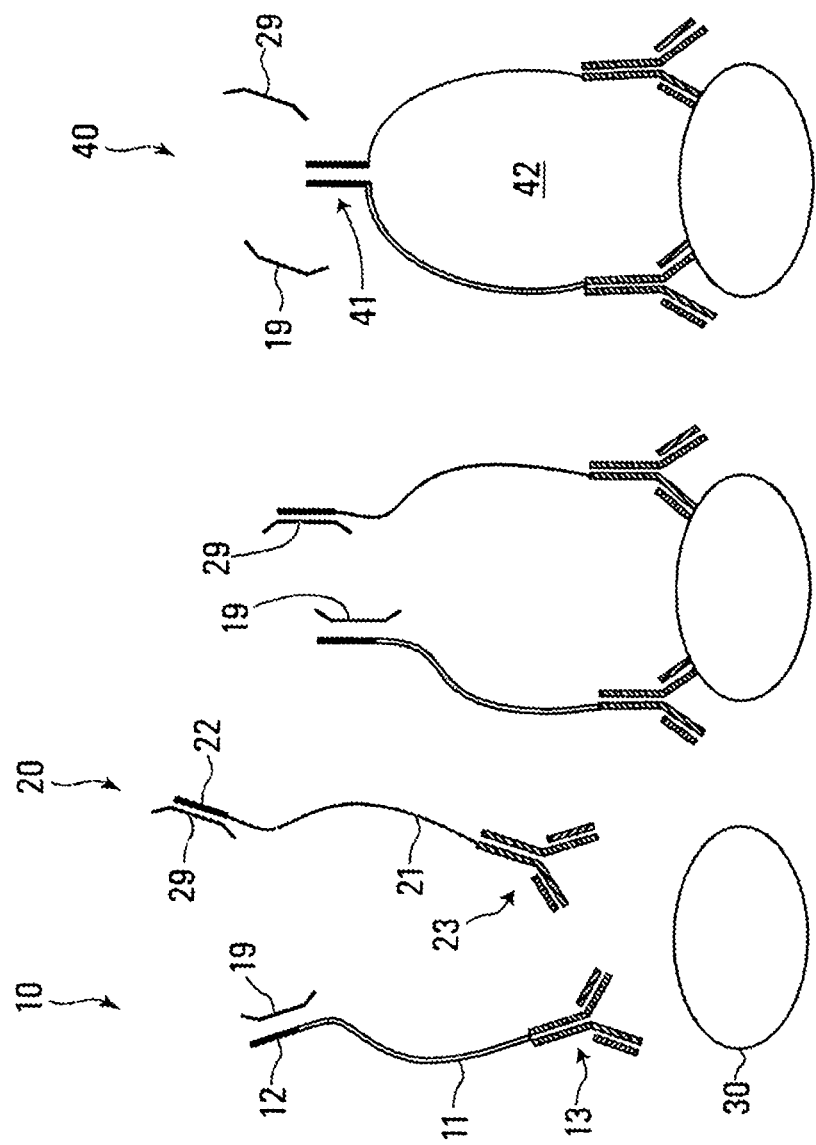
FIG. 2. Another embodiment of the binding-induced hairpin detection system. Similar to FIG. 1 except here, blocking oligonucleotides have been added in (A) to reduce background hybridization. When a first and second probe are in proximity by binding to a single target molecule (or to two or more associated molecules) in (B), the free ends of the probes hybridize, displacing the blocking oligonucleotides, forming a binding-induced hairpin (C).

In another embodiment, a detection system of the invention may be used to detect a target molecule, forming a binding-induced hairpin as follows: see FIG. 2: Similar to the above description of FIG. 1 except here, blocking agents have been added in (A) to reduce background hybridization. Depicted in this figure are blocking oligonucleotides, but other blocking agents as described herein may be used in the context of the invention. In this embodiment, blocking oligonucleotide 19 has been added to block hybridization to nucleotides at the free end 12 of the oligonucleotide of the first probe 10; and blocking oligonucleotide 29 has been added to block hybridization to nucleotides at the free end 22 of the oligonucleotide of the second probe 20. Once a first probe and a second probe bind to a single target molecule (or to two or more associated molecules) in (B), nucleotides at the free end 12 of first probe 10 may hybridize to complementary nucleotides at the free end 22 of second probe 20, displacing blocking oligonucleotides 19 and 29, forming a hairpin stem 41, thereby forming a binding-induced hairpin 40 (C).

Figure 3:
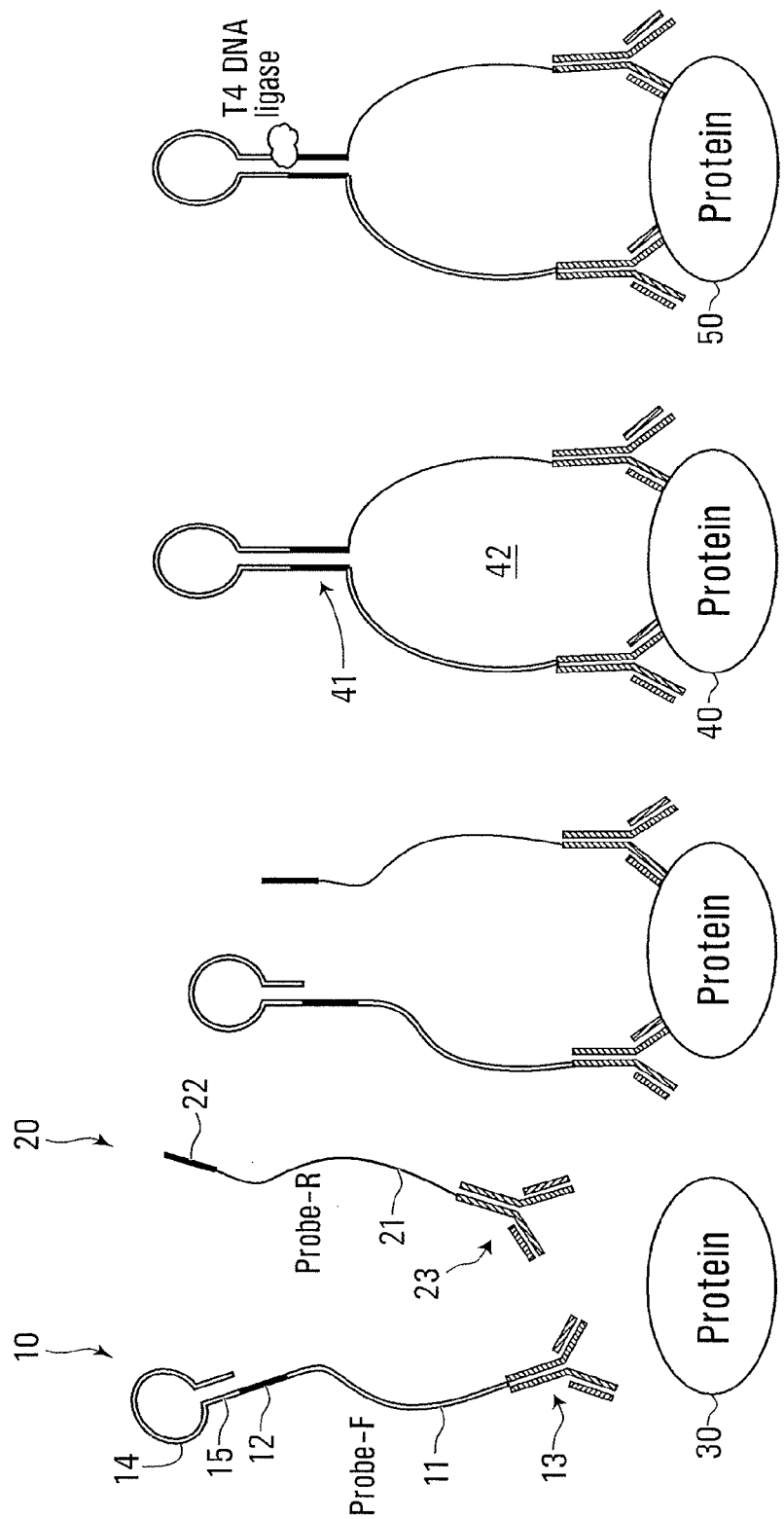
FIG. 3. Another embodiment of the binding-induced hairpin detection system. Similar to FIG. 1 except here, in (A) the oligonucleotide of the first probe further comprises a hairpin. In this regard, the free end of the oligonucleotide of the first probe further comprises regions of complementarity that allow the end of the oligonucleotide to fold back and basepair to form a hairpin loop and stem. Following the binding of first and second probes to a single target molecule (or to two or more associated molecules) in (B), the free end of the oligonucleotide of the second probe hybridizes near the free end of the oligonucleotide of the first probe, forming a hairpin stem, thereby forming a binding-induced hairpin (C). Due to the presence of a pre-existing hairpin at the free end of the oligonucleotide of the first probe, the formation of the binding-induced hairpin places the free end of the first probe adjacent to the free end of the second probe (D). As configured, the ends of the oligonucleotides of the first and second probes may be ligated together to form a new, continuous and amplifiable oligonucleotide.

In another embodiment, a detection system of the invention may be used to detect a target molecule, forming a binding-induced hairpin as follows: see FIG. 3: (A). A first probe 10 and a second probe 20 are used to bind to target molecule 30. Target molecule 30 may be a single molecule or two or more associated molecules. In this embodiment, the free end of the oligonucleotide of the first probe 10 further comprises regions of complementarity 15 and 16 that allow the end of the oligonucleotide to fold back and base-pair to form a hairpin loop 14 and stem 15+16. Targeting molecules 13 and 23 are merely depicted as antibodies, but may be any targeting molecule as described herein. In the absence of targets, the first and second probes are typically present separately. The length of stem sequences may be short enough so that the free probes typically do not hybridize together. (B) In the presence of target molecules, a first probe and a second probe bind to a single target molecule (or to two or more associated molecules), placing the two probes in proximity. (C) As a result, nucleotides at the free end 22 of the oligonucleotide of the second probe 20 may hybridize to complementary nucleotides near the free end 12 of the oligonucleotide of the first probe 10, forming a hairpin stem 41, thereby forming a binding-induced hairpin structure 40. In this embodiment, 16 is at the end of the oligonucleotide of the first probe; and 12 is near the free end of the oligonucleotide of the first probe. The term "near" is not limited by any specific distance away from the end of the oligonucleotide. A nucleotide that is near the end of the oligonucleotide may be at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 35, at least 40, at least 45, at least 50, at least 60, at least 70 or more nucleotides away from the last (terminal) nucleotide at the free end of an oligonucleotide. Typically, "near" refers to nucleotides that are adjacent to the pre-existing hairpin of a probe. The nonhybridized portions of the first and second probes 11 and 21, together with the targeting molecules 13 and 23, and the target molecule (or the two or more associated molecules) bound thereto 30, form the hairpin loop 42 of the binding-induced hairpin. In this embodiment, the oligonucleotide of the first probe comprises a pre-existing hairpin, i.e. loop 14, and stem 15+16. Thus hybridization of nucleotides at the free end 22 of the oligonucleotide of the second probe 20 to complementary nucleotides near the free end 12 of the oligonucleotide of the first probe 10 results in the formation of two hairpin loops (14 and 42) with a common hairpin stem (15, 16 and 41). (D) The formation of the binding-induced hairpin places the free end 16 of the first probe adjacent to the free end 22 of the second probe, both complementary to the other arm, allowing these free ends to be joined by enzymatic DNA ligation (e.g. by a ligase, such as T4 DNA ligase). This approach does not require, for example, the presence of a connector molecule in order to ligate the ends of the first and second probes. This results in a binding-induced hairpin comprising a single oligonucleotide 50. Detection of new oligonucleotide correlates with the presence of the target molecule.

Figure 4:
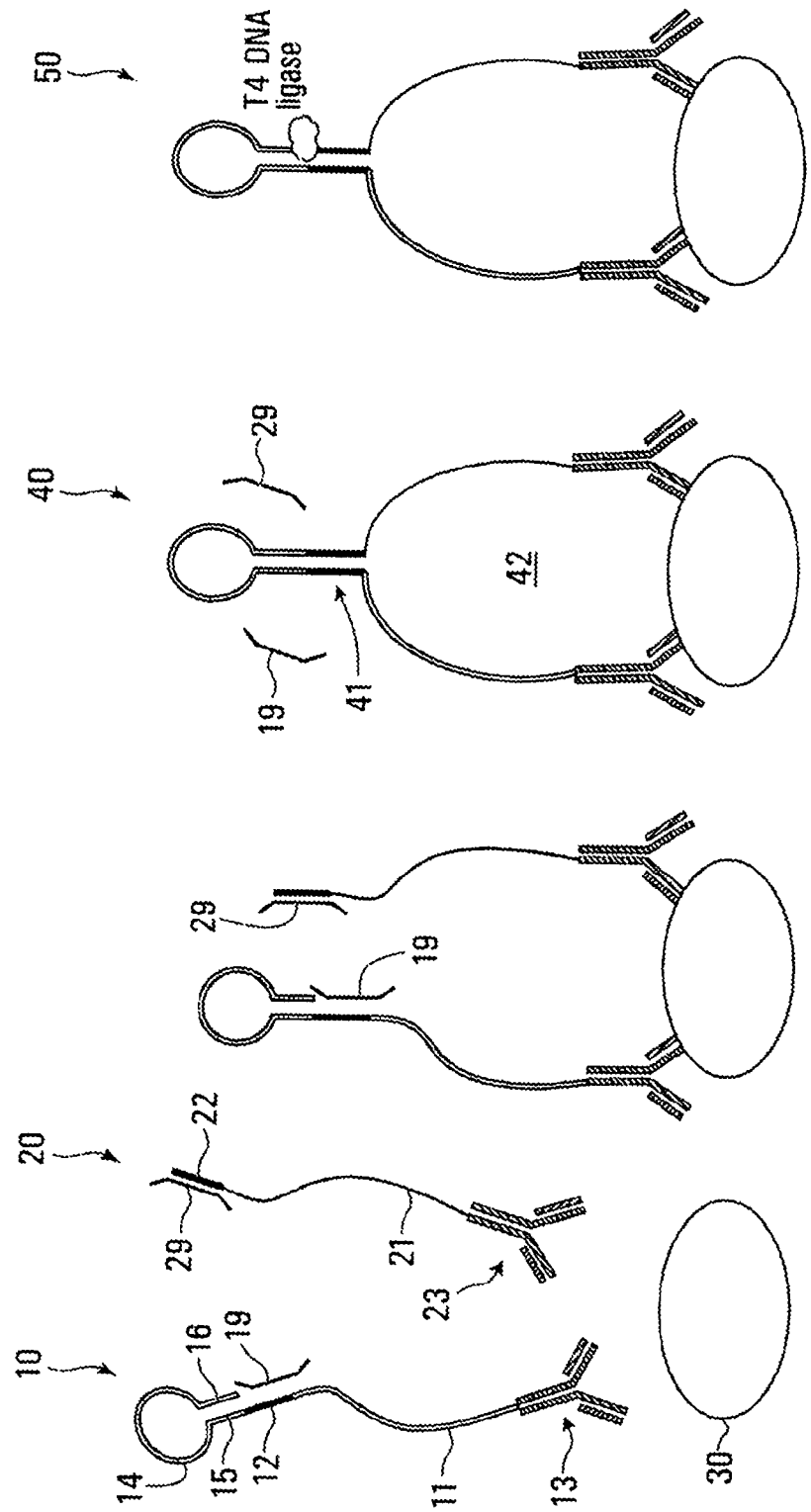
FIG. 4. Another embodiment of the binding-induced hairpin detection system. Similar to FIG. 3 except here, blocking oligonucleotides have been added in (A) to reduce background hybridization. When a first and second probe are in proximity by binding to a single target molecule (or to two or more associated molecules) in (B), the first and second probes may hybridize, displacing the blocking oligonucleotides, forming a binding-induced hairpin (C). Once the binding-induced hairpin is formed, the free end of the first probe may be ligated to the free end of the second probe, forming a new, continuous and amplifiable oligonucleotide (D).

In a further embodiment, a detection system of the invention may be used to detect a target molecule, forming a binding-induced hairpin as follows: see FIG. 4: Similar to the above description of FIG. 3 except here, blocking agents have been added in (A) to reduce background hybridization. Depicted in this figure are blocking oligonucleotides, but other blocking agents as described herein may be used in the context of the invention. In this embodiment, blocking oligonucleotide 19 has been added to block hybridization to the free end 12 of the first probe 10; and blocking oligonucleotide 29 has been added to block hybridization to the free end 22 of the second probe 20. Once the first and second probes bind to a single target molecule (or to two or more associated molecules) in (B), nucleotides at the free end 22 of the oligonucleotide of the second probe 20 hybridize to nucleotides near the free end 12 of the oligonucleotide of the first probe 10, displacing blocking oligonucleotides 19 and 29, forming a hairpin stem 41, thereby forming a binding-induced hairpin 40 (C). Once the binding-induced hairpin 40 is formed, the free end 16 of the first probe may be ligated to the free end 22 of the second probe, forming a new, continuous and amplifiable oligonucleotide 50 (D).

A symmetrical binding-induced hairpin is depicted in FIGS. 1-4. However, it is not necessary for the hairpin structure to be symmetrical. It may be asymmetrical, that is, one probe is longer than the other. The asymmetry may not affect the stability of the binding-induced hairpin.

When the first and second probes are brought into proximity, for example by binding to the same target molecule (or to two or more associated molecules), the free end of the oligonucleotide of the first probe may hybridize to the free end of the oligonucleotide of the second probe, forming a binding-induced hairpin. However, if the free end of the oligonucleotide of the first probe comprises a hairpin, hybridization of the probes upon binding to a target molecule may result in a structure comprising two hairpins, i.e. 1) the pre-existing hairpin on the free end of the first probe; and 2) the binding-induced hairpin that includes the bound target molecule and the two probes (forming the loop) and the hybridized free ends (forming the stem).

Upon hybridization of the probes following binding to a target molecule (or to two or more associated molecules), a stem of the binding-induced hairpin may be formed, or if the free end of the oligonucleotide of the first probe comprises a pre-existing hairpin, its stem may be extended. In either case, the hairpin stem, either newly formed or simply extended, may comprise a sequence of at least 3, at least 4, at least 5, at least 6, at least 7, at least 8, at least 9, at least 10, at least 11, at least 12, at least 13, at least 14, at least 15, at least 16, at least 17, at least 18, at least 19, at least 20 or more paired nucleotides. Preferably, the stem may comprise 5 to 10 paired nucleotides. However, the skilled person would appreciate that the length of the stem may be affected by the composition of nucleotides at the stem (GC content) and the length of loop; and may be varied as needed.

In an embodiment of the invention, this stem may contain no mismatched nucleotides. In other embodiments, this stem may contain at most 1, at most 2, or at most 3 pairs of non-complementary (mismatch) nucleotides.

Hybridization of the ends of the oligonucleotides of the first and second probes upon binding to a target molecule forms a binding-induced hairpin. The loop of the binding-induced hairpin may comprise at least 20, at least 25, at least 30, at least 35, at least 40, at least 45, at least 50, at least 55, at least 60, at least 65, at least 70, at least 75, at least 80, at least 85, at least 90, at least 95, at least 100, at least 105, at least 110, at least 115, at least 120, at least 125, at least 130, at least 135, at least 140, at least 145, at least 150, at least 155, at least 160, at least 165, at least 170, at least 175, at least 180, at least 185, at least 190, at least 195, at least 200 or more nucleotides. Preferably, the size of the loop, i.e. non-hybridized oligonucleotide portion a first and second probes may be from 30-100 nucleotides. In one embodiment, the loop of a binding-induced hairpin comprises 77 nucleotides. However, the skilled person would appreciate that the length of the loop may vary depending on the size of target molecule and targeting molecule.

Typically, the pre-existing loop on the free end of the first probe does not change in size following hybridization with the free end of a second probe.

The hybridization of the oligonucleotides of the first and second probes forms the stem of the binding-induced hairpin. Where the oligonucleotide of the first probe comprises a hairpin, the hybridization of the oligonucleotides will extend the stem of the pre-existing hairpin. The stem sequences in the oligonucleotides of probes may play a crucial role in the determination of the sensitivity of analysis. The length and G-C content of the stem sequences may be determined by a combination of theoretical estimation and experimentation. After optimization, the stem sequences need only minor adjustments for various assays. Because of the longer complementary sequence of blocking nucleotides and their higher concentrations present in solution, the blocking oligonucleotides could effectively reduce the independent background hybridization of free probes, thereby eliminating the interference of background.

Blocking Agents

A blocking agent may be used to block, directly or indirectly, the free end of oligonucleotides of the first and/or second probes. The blocking agent may be any agent that reduces and/or prevents background hybridization of the oligonucleotides.

For example, the blocking agent may be a blocking oligonucleotide. A blocking agent may block directly or indirectly the sequences which are complementary between the oligonucleotides of the first and/or second probes. In one embodiment, the blocking agent may comprise a blocking oligonucleotide that may hybridize in whole or in part to the portion of the oligonucleotide of the first probe that is complementary to that of the second probe. In another embodiment, the blocking agent may comprise a blocking oligonucleotide that may hybridize in whole or in part to the portion of the oligonucleotide of the second probe that is complementary to that of the first probe. In a further embodiment, the blocking agent may comprise a blocking oligonucleotide that may hybridize in whole or in part to the portion of the oligonucleotide of the first probe that is complementary to that of the second probe; and a blocking oligonucleotide that may hybridize in whole or in part to the portion of the oligonucleotide of the second probe that is complementary to that of the first probe.

A blocking oligonucleotide may be of any composition and length that is suitable for use in reducing and/or preventing background hybridization of the probes. Without limitation, a blocking oligonucleotide may comprise at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25 or more nucleotides. The blocking oligonucleotide may comprise DNA, RNA, synthetic nucleotides, non-natural nucleotides, altered nucleotides, or combinations of one or more thereof.

A blocking oligonucleotide may hybridize to a probe based on sequence complementarity. In one embodiment, the blocking oligonucleotide may comprise a sequence that is complementary to at least 3, at least 4, at least 5, at least 6, at least 7, at least 8, at least 9, at least 10, at least 11, at least 12 nucleotides of the oligonucleotide of a probe. In another embodiment, the blocking oligonucleotide may comprise a sequence that is complementary to at least 3, at least 4, at least 5, at least 6, at least 7, at least 8, at least 9, at least 10, at least 11, at least 12 contiguous nucleotides of the oligonucleotide of a probe.

A skilled person would appreciate that the blocking agent may reversibly block the hybridization of the probes. A blocking agent of the invention is not permanently attached to a probe (i.e. by cross-linking or covalent bond), and thus blocking of a probe may be reversed. For example, a blocking agent may be a blocking oligonucleotide that hybridizes to a probe. The blocking oligonucleotide may dissociate from the probe due to conditions, such as, elevated temperatures and/or through random motion (i.e. association/disassociation) of molecules. Thus upon binding of the probes to a target molecule, the first and second probes may be brought in proximity to one another and may hybridize, extending the hairpin stem and forming a binding-induced hairpin.

Methods of Detecting a Target Molecule

A detection system of the invention may be used in methods to detect a target molecule in a sample. For example, the method may comprise providing a sample; incubating the sample with a detection system of the invention; and detecting the binding-induced hairpin.

Providing a Sample

A detection system of the invention may be used in methods to detect a target molecule in any sample. A sample suitable for use in the context of the invention may be any substance that may or may not comprise a target molecule. In embodiments of the invention, a sample may be in liquid, solid or gaseous form.

In one embodiment, the sample may comprise any liquid, solid or gas derived from, without limitation, a species from the kingdoms Monera, Protista (Protoctista), Fungi, Plantae, and Animalia. A preferred group of samples may include, without limitation, a fluid (e.g. blood, spinal, lymph), an extract, a homogenate, a protein, a nucleic acid, a lipid, a cell or a tissue from an animal, a bird, a fish, a human, a plant or a fungi. In other embodiments, the sample may be derived from an inorganic, artificial or synthetic source.

Incubation of Sample with a Detection System

A detection system of the invention may be incubated with a sample to detect a target molecule. An incubation medium and incubation conditions may be used to incubate the detection system and the sample.

In one embodiment, the detection system and the sample may be incubated in any medium that allows the detection system and the target molecule to interact, for example by contact, to form a binding-induced hairpin. For example, the incubation medium may be a buffer, such as PBS.

The detection system and a sample may be incubated in a medium under conditions suitable for interaction between the detection system and the target molecule. In one embodiment, the detection system and the sample may be incubated at a temperature that discourages the hybridization of free probes but favours the hybridization of probes bound to its target molecule and thus for formation of a binding-induced hairpin. In another embodiment, the detection system and the sample may be incubated in conjunction with one or more blocking agents. Addition of blocking agents may reduce and/or prevent background hybridization. For example, the probes may be incubated with one or more blocking agents prior to, simultaneously with, or after the addition of a sample.

The detection system and the sample may be incubated in conjunction with a ligase. A ligase may be added to join the ends of hybridized probes thus forming a single oligonucleotide. This may, for example, assist in detecting the target molecule.

Detecting the Binding-Induced Hairpin

The skilled person would understand that routine approaches may be used to detect the binding-induced hairpin structure as an indication of the presence of a target molecule in a sample.

In one embodiment, the ends of oligonucleotides may be ligated after formation of the binding-induced hairpin, forming a continuous oligonucleotide. Typically, the probes and incubation conditions used favour the hybridization and ligation of probes that are held in proximity by way of binding to a target molecule. Detection methods that can distinguish between ligated and non-ligated ends may be used to indirectly detect the target molecule, such as, Polymerase Chain Reaction (PCR) or Real time PCR.

Polymerase chain reaction (PCR) (U.S. Pat. Nos. 4,683, 195; 4,683,202; and 4,965,188) is a process that is used to increase the concentration of a target nucleic acid sequence in a sample. The method typically involves the use of forward and reverse primers that are complementary to the target sequence to amplify the target sequence; and a cycle of three temperatures to promote denaturation, annealing and extension. PCR may discriminate binding-induced hairpins in which the ends are ligated from those that are not due to the inability of polymerase to traverse a discontinuous template.

Real time PCR is based on the principle of PCR but allows the reliable detection and quantification of nucleic acid sequences. PCR reactions may be divided into three segments: an exponential phase, a linear phase and a plateau phase. Theoretically, during the exponential phase, there is a quantitative relationship between the amount of starting target sequence and the amount of PCR product at any given cycle. Within the exponential phase, a real-time PCR instrument calculates two values. The Threshold line is the level of detection at which a reaction reaches a fluorescent intensity above background. The PCR cycle at which the sample reaches this level is called the Cycle Threshold, Ct. The Ct value is used in quantitation or presence/absence detection analysis. By comparing the Ct values of samples of unknown concentration with a series of standards, the amount of template DNA in an unknown reaction can be accurately determined.

Real time PCR relies on the nuclease activity of the polymerase and the use of a reporter molecule that binds to the amplification product. Common reporter molecules include, without limitation, (1) the use of fluorescent dyes that intercalate with double-stranded DNA, and (2) modified DNA oligonucleotide probes that fluoresce when hybridized with a complementary DNA. For example, the reporter molecule may comprise a labeled oligonucleotide that binds a target to be amplified (template). The labeled oligonucleotide may comprise a fluorescent molecule at one end and a quenching molecule at the other, which quenches the fluorescence of the fluorescent molecule. As the polymerase traverses the template, it will reach and cleave the fluorescent molecule from the labeled oligonucleotide. The fluorescence of the cleaved fluorescent molecule may be detected. The amount of fluorescence is directly proportional to the amount of template/per product produced.

Approaches to detect the binding-induced hairpin structure are not limited to ligation mediated assays. For example, many fluorescence techniques may be employed to monitor the hairpin formation. In one embodiment, a pair of fluorophores or quantum dots is attached to the free ends of the first and second probes; therefore, the formation of the hairpin structure would be amenable for Förster resonance energy transfer (FRET). FRET involves the use of a donor chromophore, initially in its electronic excited state, that may transfer energy to an acceptor chromophore (in proximity, typically less than 10 nm) through nonradiative dipole-dipole coupling. This transfer of energy is detectable and in the context of the invention may be used to detect the hybridization of the first and second probes. In another embodiment, stem formation of binding-induced hairpin may be detected by double-stranded DNA dyes, such as SYBR green.

The detection system of the invention may be used to detect and/or quantitate the amount of a target molecule in a sample. In embodiments of the invention, a detection system of the invention may effectively detect fewer than 500, fewer than 450, fewer than 400, fewer than 350, fewer than 300, fewer than 250, fewer than 200, fewer than 175, fewer than 150, fewer than 125, fewer than 100, fewer than 90, fewer than 80, fewer than 70, fewer than 60, fewer than 50, fewer than 40, fewer than 30 or fewer than 20 molecules per microliter of a sample.

In another embodiment, a detection system of the invention may effectively detect less than $1\times10^{-9}$, less than $1\times10^{-10}$, less than $1\times10^{-11}$, less than $1\times10^{-12}$, less than $1\times10^{-13}$, less than $1\times10^{-14}$, less than $1\times10^{-15}$, less than $1\times10^{-16}$, or less than $1\times10^{-17}$ M of a target molecule in a sample.

The skilled person would appreciate that the detection limit of the detection system of the invention may vary depending on the method used to detect the binding-induced hairpin.

Uses of the Detection System

A detection system of the invention may have research, medical and industrial applications. In one embodiment, a detection system of the invention may be used to detect the presence or absence of a target molecule in a sample. For example, a detection system of the invention may be used to detect the presence of a disease associated antigen (e.g. PSA) in the diagnosis of a patient. In another embodiment, a plurality of detection systems of the invention may be used to detect a plurality of distinct target molecules, wherein each detection system of the plurality of detection systems has a distinct target specificity. Of course, each targeting molecule of each of the first and second probes of each detection system may also have distinct target specificities.

In another embodiment, a detection system of the invention may be used to quantitate the amount of a target molecule in a sample. For example, a detection system of the invention may be used to quantitate the amount of a toxin in a water sample; or the levels of a growth factor (e.g. PDGF) in an animal.

In another embodiment, a plurality of detection systems of the invention may be used to simultaneously detect a plurality of distinct target molecules in a sample. For example, multiple detection systems, each with specificity for a distinct target molecule may be used to detect and/or quantitate the levels of multiple isoenzymes that cause fruit browning in a sample of fruit.

In another embodiment, a detection system of the invention may be used to monitor a dynamic event. For example, the events that allow two probes to be brought together in a single complex molecule, such as the interaction of two biomolecules, could be monitored by detecting the binding-induced hairpin. In another example, a detection system of the invention may be used to identify novel interactions between biomolecules. This may be achieved by targeting a first probe to a first biomolecule and targeting the second probe to a novel biomolecule or to a target not previously known to interact with the first biomolecule; incubating them together; and detecting for the presence of a binding-induced hairpin. In this regard, multiple probes to multiple novel target molecules may be used to determine which, if any, interacts with the first biomolecule. These multiple probes may be distinguished using probes comprising unique oligonucleotide sequences.

In embodiments of the invention, a detection system of the invention may be used in vivo, in situ, in vitro or ex vivo to detect a target molecule.

Kits and commercial packages comprising the detection system described herein are contemplated. Such a kit or commercial package may contain instructions regarding use of the included detection system, for example, to detect a target molecule in a sample in accordance with the methods described herein. The kit or commercial package may also contain reagents' suitable for using a detection system of the invention. Suitable reagents may include, but are not limited to, buffers (e.g. PBS, buffers and reagents suitable for PCR or real time PCR, a buffer suitable for an enzymatic reaction, such as ligation by DNA ligase); pharmaceutically acceptable carriers, diluents and excipients (e.g. as described in Remington's Pharmaceutical Sciences 16th edition, Osol, A. Ed. (1980)); adjuvants; blocking agents; ligases (e.g. T4 DNA ligase); and preservatives.

The invention is further illustrated by the following, non-limiting examples.

EXAMPLES

Experimental

Reagents

PDGF-AA, PDGF-AB, PDGF-BB, and biotinylated polyclonal anti-prostate specific antigen (PSA) antibody were obtained from R&D System (Minneapolis, Minn.). Streptavidin, PSA, BSA, goat serum, and biotin were obtained from Sigma-Aldrich (Oakville, ON). SYBR GreenER qPCR Supermix Universal was obtained from Invitrogen Canada (Burlington, ON). PDGF-BB binding aptamer (5'-/Biotin/ TTTTTTTTTTTACTCAGGGCACTGCAAG-CAATTGTGGTCCCAATGGGCTGAGT AT-3') (SEQ ID NO: 1) was synthesized by Integrated DNA Technologies (Corarville, Iowa). It was labeled at the 5' end with a biotin group and purified by reversed-phase HPLC. Table 1 lists the oligos used in this study. These oligos are all synthesized, labeled, and purified by Integrated DNA Technologies. The oligo of Probe-F was attached with a biotin group at the 5' end, and oligos of Probe-R were labeled with a phosphate group at the 5' end and a biotin group at the 3' end. The stem sequences are underlined in the oligos of Probe-F and Probe-R. The stem sequence of the oligo of Probe-R5, 6, 7, and 8 contains 5, 6, 7, and 8 complementary bases, respectively. Block-R6 was used in the assay when probe-R was constructed from oligos of Probe-R6, while Block-R7 was used when Probe-R was constructed from oligos of Probe-R7. Underlined sequences of Block-F and R are complementary to the corresponding sequences of the oligos of Probe-F and R, respectively. The 1× Phosphate buffered saline (PBS) (137 mM NaCl, 10 mM phosphate, 2.7 mM KCl, pH 7.4) was diluted with deionized water from 10×PBS buffer (from Fisher Scientific, Nepean, ON). All other reagents were commercially available analytical grade.

Preparation of Binding-Induced Hairpin Probes

Since the 5' end of oligos of Probe-F and the 3' end of oligos of Probe-R were labeled with biotin, oligos of Probe-F and Probe-R were directly used as probes (Strep-Probe-F and Strep-Probe-R) for streptavidin analysis. Probes named as PDGF-Probe-F or PDGF-Probe-R for PDGF-BB analysis were prepared by incorporation of the oligos of Probe-F or Probe-R into the biotinylated aptamer through streptavidin biotin interaction. 100 μL 200 nM oligo of Probe-F or R and 100 μL 200 nM streptavidin, diluted in 1×PBS, were first mixed and incubated at 37° C. for 1 h. 100 μL of the above solution was then added to 100 μL of 100 nM biotinylated aptamer diluted in 1×PBS. The mixture was incubated at 37° C. for another 1 h forming PDGF-Probe F or R. The PDGF-Probe F or R solution was then diluted to 10 nM in 1×PBS buffer containing 1% BSA and 10 mM biotin, and stored at 4°

C. The preparation of probes (PSA-Probe-F and PSA-Probe-R) for analysis of PSA was a similar process to that of probes for analysis of PDGF-BB, except that the solutions were incubated at room temperature for 1 h instead of at 37° C., and biotinylated polyclonal anti-PSA antibody (R&D System) replaced the biotinylated aptamer.

Cell Lysate and Serum Sample Preparation 1.5 ml of medium containing approximately $2\times10^6$ Vero 76 monkey kidney cells was spun at 10,000 g for 3 min. After being washed three times with cold 1×PBS, the pellet was resuspended in 250 μL ice-cold lysis buffer containing 50 mM Tris (pH 7.4), 150 mM NaCl, 1% Triton X-100, 1%

TABLE 1

Summary of oligonucleotides (oligos) used in this study

| Oligos | Sequences (5' → 3') |
|---|---|
| Oligo of Probe-F | ACTGTGTCTCGTCGTTGGTGTTTTGTTTTGTTTTAGGCTGGTCG CTTTGTTTTGCGAC (SEQ ID NO: 2) |
| Oligo of Probe-R5 | CAGCCCTTTGTTTGTTTTGTTTTTTTGATGGAGCAGGTGTCAGA TC (SEQ ID NO: 3) |
| Oligo of Probe-R6 | CAGCCTTTTGTTTGTTTTGTTTTTTTGATGGAGCAGGTGTCAG ATC (SEQ ID NO: 4) |
| Oligo of Probe-R7 | CAGCCTATTTTGTTTGTTTTGTTTTTTTGATGGAGCAGGTGTCA GATC (SEQ ID NO: 5) |
| Oligo of Probe-R8 | CAGCCTAATTTTGTTTGTTTTGTTTTTTTGATGGAGCAGGTGTC AGATC (SEQ ID NO: 6) |
| Block-F-1 | TTTGCCTAAAATTT (SEQ ID NO: 7) |
| Block-F-2 | TTTGCCTAAAACTTT (SEQ ID NO: 8) |
| Block-F-3 | TTTGCCTAAAACATTT (SEQ ID NO: 9) |
| Block-F-4 | TTTGCCTAAAACAATTT (SEQ ID NO: 10) |
| Block-F-5 | TTTGCCTAAAACAAATTT (SEQ ID NO: 11) |
| Block-R6-1 | TTTAAAGGCTGTTT (SEQ ID NO: 12) |
| Block-R6-2 | TTTAAAAGGCTGTTT (SEQ ID NO: 13) |
| Block-R6-3 | TTTAAAAAGGCTGTTT (SEQ ID NO: 14) |
| Block-R6-4 | TTTCAAAAGGCTGTTT (SEQ ID NO: 15) |
| Block-R7-1 | TTTAATAGGCTGTTT (SEQ ID NO: 16) |
| Block-R7-2 | TTTAAATAGGCTGTTT (SEQ ID NO: 17) |
| Block-R7-3 | TTTAAAATAGGCTGTTT (SEQ ID NO: 18) |
| Block-R7-4 | TTTCAAAATAGGCTGTTT (SEQ ID NO: 19) |

Analysis of Streptavidin, PDGF-BB, and PSA

The procedures for analysis of streptavidin, PDGF-BB, and PSA proteins are similar and are thereby described together. Unless otherwise indicated, a 20 μL of 1×PBS (with 1 mM MgCl$_2$ for PDGF-BB) solution, containing 100 μM Probe-F and Probe-ft 100 nM Block-F and Block-R, and desired amount of proteins, was incubated at 37° C. for 30 min and then at room temperature for another 10 min. An aliquot (2 μL) of the above solution was then transferred into a real-time PCR reaction tube (Applied Biosystems (ABI), Foster City, Calif.). After addition of the reagents for ligation and amplification, the final 20 μL reaction solution contained 100 μM ATP, 0.4 Unit T4 DNA ligase (Invitrogen), 0.1 μM primers (forward and reverse), ROX reference dye, and 10 μL SYBR GreenER qPCR Supermix Universal (Invitrogen, Burlington, ON). After 10 min ligation reaction at room temperature, the reaction vials were transferred into a real-time PCR instrument (ABI 7500 Fast Real-Time PCR System). The PCR program consisted of 50° C. for 2 min, 95° C. for 6 min, followed by 50 cycles of 95° C. for 15 s, 60° C. for 60 s.

NP-40, 0.1% SDS and 0.5 mM PMSF. The lysate were spun at 15,000 g for 10 min at 4° C. The supernatant was carefully transferred into another tube and diluted two-fold by 1×PBS containing 2 mM MgCl$_2$. When not analyzed immediately, the cell lysate was stored at 4° C.

The frozen serum was thawed in a water bath at 30° C., and then kept on ice. Prior to analysis, 0.5 ml serum was centrifuged at 10,000 rpm for 10 min to remove solid particles. The appropriate volumes of PSA stock solutions were mixed with 2.5 μL serum to obtain the desired concentration, and 1×PBS was then used to produce a final volume of 50 μL.

Results

Design and Construction of Binding-Induced Hairpin Probes

A pair of probes, Probe-F and Probe-R, were constructed in this experiment. Both probes were ligand-DNA conjugates. Ligands in probes can be small or macromolecules that are able to bind to the single target molecule. The ligands used in this study included biotin for detection of streptavidin, aptamers for PDGF-BB, and antibodies for PSA.

Oligos were conjugated to the ligands by different approaches. The 5' end of oligos was attached to ligands in Probe-F, while the 3' end of oligos was attached to ligands for Probe-R. In the first example of detecting streptavidin, biotin was covalently linked to the ends of oligos. In the case of detecting PSA, antibody for PSA was first biotinylated, and then the biotinylated oligos were conjugated to the antibody by using streptavidin as a connector. Likewise, in the experiments of detecting PDGF, the aptamer for PDGF was first biotinylated, and then the biotinylated oligos were conjugated to the aptamer by using streptavidin as a connector. Although aptamers can be extended directly with additional oligo bases, the approach used in the present study using biotin-streptavidin chemistry offers two advantages. The streptavidin not only works as a connector, it also serves as a spacer that could potentially reduce the effect of extended oligos on the favorable secondary conformation of the aptamer. The use of two shorter oligos makes their synthesis easier than having to preparing for a longer oligo.

The oligo in Probe-F was designed to possess a hairpin structure at its free end. This hairpin structure was created with strong stability, providing one side of the strand for subsequent DNA ligation. A piece of stem sequence was placed next to the hairpin structure. This sequence was used to hybridize the other stem sequence at the free end of the oligo in Probe-R when the binding-induced hairpin was induced by the binding to the target molecule. In order to facilitate DNA ligation, a phosphate group was attached to the free end of the oligo in Probe-R.

The principle of using binding-induced hairpin assay for protein analysis may be expressed in the following equations. Equation 1 describes the process of inducing a hairpin structure through the binding of two probes to the target molecule:

$$\text{Probe-}F + \text{Probe-}R + T \xrightleftharpoons{K_1} \text{Probe-}F \cdot T \cdot \text{Probe-}R_{open} \xrightleftharpoons{K_2} \text{Probe-}F \cdot T \cdot \text{Probe-}R_{close} \quad (1)$$

Where T is the target molecule; Probe-F·T·Probe-$R_{open}$ is the complex of Probe-F, Probe-R, and target in the form of random coil; Probe-F·T·Probe-$R_{close}$ is the complex of Probe-F, Probe-R, and target in the form of hairpin structure; and $K_1$ and $K_2$ are equilibrium constants,
In the absence of target, Probe-F may also hybridize to Probe-ft producing background.

$$\text{Probe-}F + \text{Probe-}R \xrightleftharpoons{K_3} \text{Probe-}F \cdot \text{Probe-}R \quad (2)$$

Where Probe-F·Probe-R is the background (target-independent) hybrid of Probe-F and Probe-R.
While Probe-F·T·Probe-$R_{close}$ is the desired complex that yields the subsequent signal for target detection, Probe-F·Probe-R produces background interfering with the detection. The signal to background ratio of the method can be expressed as follows:

$$\frac{\text{Signal}}{\text{Background}} = \frac{[\text{Probe-}F \cdot T \cdot \text{Probe-}R_{close}]}{[\text{Probe-}F \cdot \text{Probe-}R]} = \frac{K_1 K_2 [T]}{K_3} \quad (3)$$

The value of $K_1$ is mainly dependent on the binding affinity of probes to the targets. The probes with higher binding affinity lead to higher sensitivity of analysis. $K_2$ and $K_3$ depend mainly upon the length and G-C content of the stem sequence for forming hairpin stems. Therefore, the stem sequence can be designed to produce the best signal to background ratio.

The initial concentrations of Probe-F and -R affect the value of [T], thereby producing an impact on the sensitivity of the method. In this study, the above parameters were optimized to achieve highly sensitive detection. To improve the sensitivity further, blocking oligonucleotides were applied to reduce the background (target independent) hybridization between Probe-F and Probe-R. One pair of blocking oligonucleotides Block-F and Block-R were designed to be complementary to part or whole of the stem sequence in Probe-F and Probe-R.

Analysis of Streptavidin

To demonstrate the proof of principle, streptavidin was chosen as the initial target protein because of its extraordinarily strong affinity for biotin ($K_d=10^{-15}$M). The use of biotin-DNA conjugates as probes provided one of the strongest known non-covalent interactions, simplifying the impact of the binding affinity of probes on the sensitivity of the method. Therefore, the focus was directed to optimizing other important parameters, such as the length and G-C content of the stem sequence, the concentration of probes, the length of blocking oligonucleotides, and the ligation time.

Figure 5:
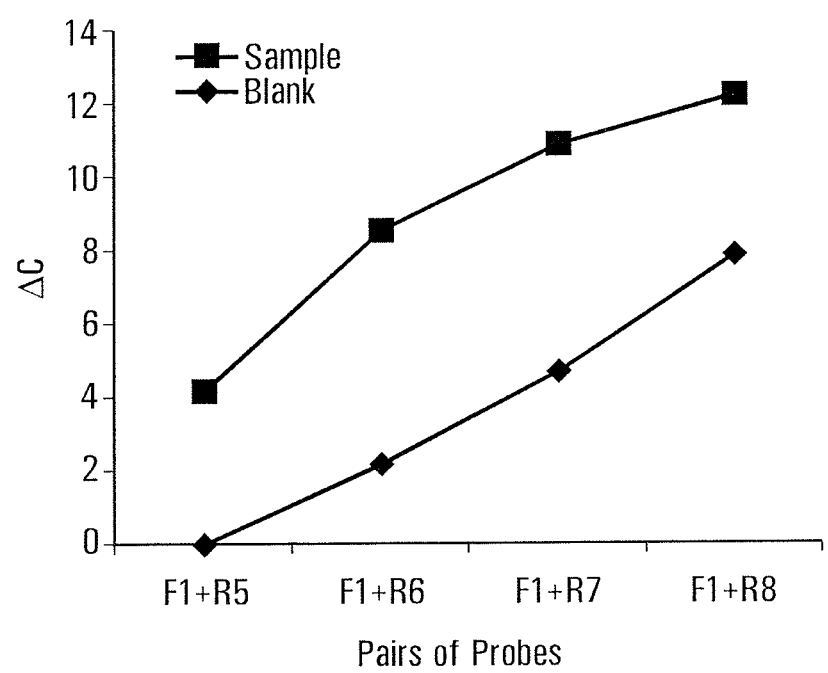
FIG. 5. Effect of the length and G-C content of stem sequence on signal and background in the formation of binding-induced hairpin. F1 represents Strep-Probe-F1. R5, R6, R7, and R correspond to Strep-Probe-R5, R6, R7, and R8. The sequences of F1, R5, F6, R7, and R8 are shown in Table 1.

The length and G-C content of the stem sequence were designed to achieve the largest $K_2/K_3$ value. That is, to obtain the highest sensitivity, the probes used should produce the lowest level of background hybridization on the basis of yielding enough percentage of probe target complex in hairpin structure. The $\Delta T_m$, the difference in melting temperature between the hairpin structure and the hybrid formed from separate probes, is an important reference parameter in design of the arm sequence for the binding-induced hairpin. Oligo-analyzer 3.1 from IDT was used to estimate the $T_m$ of hairpins with a loop containing 100-140 thymidines and the corresponding hybrids from separate nucleotides, and obtained a 5-base sequence as the starting stem sequence. Four pairs of probes containing this 5-stem base or 1-3 additional A-T base pairs were used for analysis of $10^{-13}$M streptavidin. The results are shown in FIG. 5. In order to easily compare the results under different conditions, the $\Delta C_t$ was applied as the cycle threshold with the largest value subtracting the value of the cycle threshold at each point. Therefore, the $\Delta\Delta C_t$ between sample and blank is the signal intensity of the analysis. The background or independent hybridization was increased with the increase of number of complementary bases. The probes with six complementary bases resulted in the largest differences between the sample and the blank when analyzed by real-time PCR. The use of the probe sequence F1 and R6 (Table 1) to construct Strep-Probe-F1 and Strep-Probe-R6 probes resulted in best sensitivity for streptavidin analysis.

Figure 6:
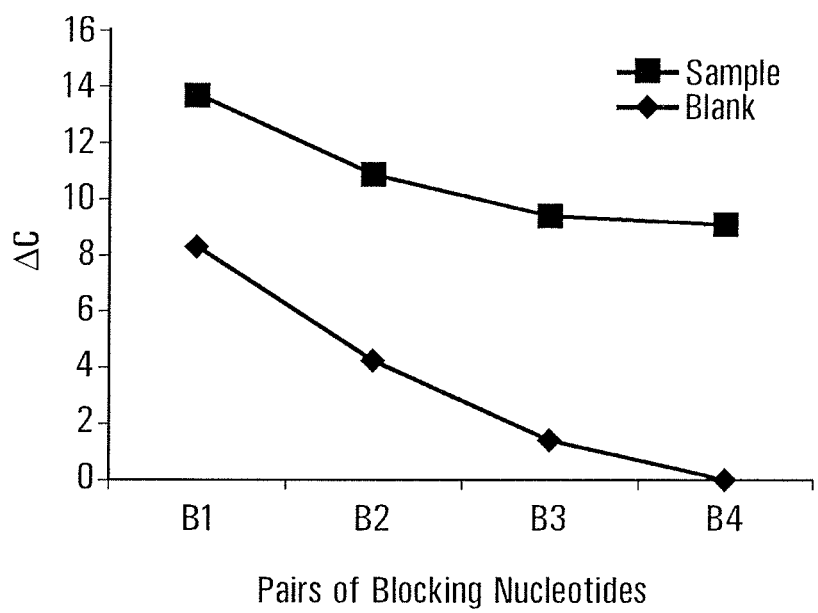
FIG. 6. Effect of the length of blocking oligonucleotides on signal and background in the formation of binding-induced hairpin. B1 represents the use of Block-F-1 and Block R6-1. B2 represents the use of Block-F-2 and Block R6-2. B3 represents the use of Block-F-3 and Block-R6-3. B4 represents the use of Block-F-4 and Block R6-4. The sequences of these blocking oligonucleotides are shown in Table 1.

Using Strep-Probe-F1 and Strep-Probe-R6 as probes, a pair of blocking oligonucleotides was applied to further decrease the background produced by independent hybridization in solution. Block-R hybridized the part containing the whole arm sequence at the free end of Probe R, whereas Block-F, hybridizing the Probe F, was designed to cover the sequence containing the arm sequence with two bases left at the 3' end to avoid the occurrence of hybridization between Block R and F. FIG. 6 shows the analysis of $10^{-13}$M streptavidin using pairs of blocking oligonucleotides with different numbers of complementary bases. The longer blocking oligonucleotide led to lower background. The pair of Block-F-4 and Block-R6-4 resulted in the largest differences in threshold cycles between the sample and the blank.

Figure 7:
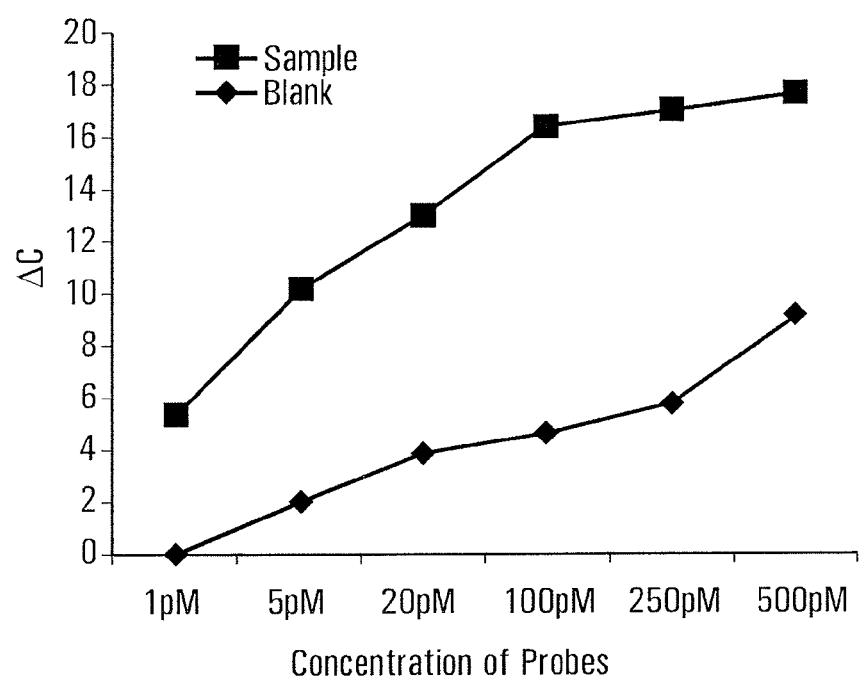
FIG. 7. Effect of the concentration of probes on signal and background in the formation of binding-induced hairpin.

The impact of probe concentration and ligation time on analysis of streptavidin ($10^{-13}$ M) was also examined. Various concentrations of Strep-Probe-F1 and Strep Probe-R6 probes from 1 pM to 500 pM were used. Although the background increased consistently with increase of probe concentrations, the increase in signal was higher until the probe concentrations reached 100 pM (FIG. 7).

Figure 8:
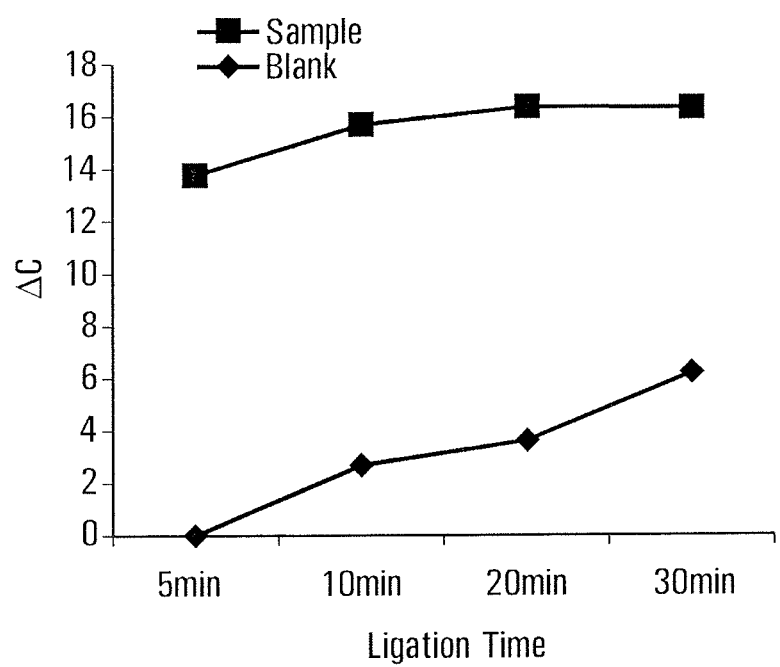
FIG. 8. Effect of the ligation time on signal and background in the formation of binding-induced hairpin.

The impact of the ligation time was studied by analysis of samples at fixed amount of streptavidin ($10^{-13}$M) or blank with various ligation times from 5 min to 30 min (FIG. 8). The longer time allowed more products of ligation, increasing the background. But the ligation time did not show much affect on the detection of streptavidin. The ligation time of 10 min was chosen for analysis of streptavidin.

Figure 9:
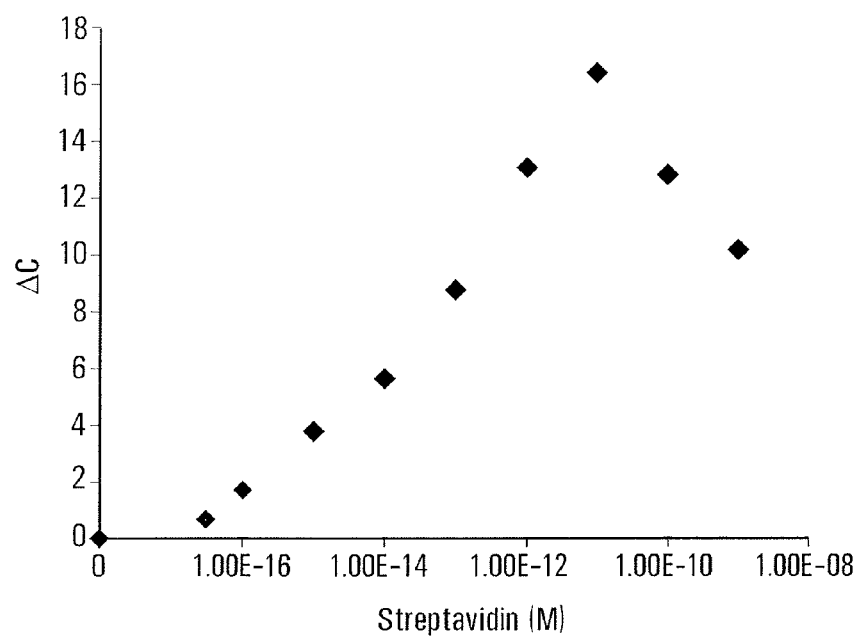
FIG. 9. Analysis of streptavidin on the formation of binding-induced hairpin.

After optimization of the above parameters, the principle was applied to analysis of solutions containing varying concentrations of streptavidin ($5\times10^{-17}$ M to $1\times10^{-9}$M) (FIG. 9). A linear dynamic range of over 5 orders of magnitude ($5\times 10^{-17}$ M to $10^{-11}$M) was obtained, and the method was able to distinguish the solutions containing protein levels at 2-fold difference. The value of $\Delta\Delta C_t$ started decreasing from $1\times 10^{-10}$M, because there were not enough probes to provide at least two molecules to bind to each streptavidin molecule when the solution contained streptavidin in excess of $1\times10^{-10}$ M. A detection limit of $3\times10^{-17}$M, defined as the concentration equivalent to three times the standard deviation of the background level, was reproducibly obtained for homogeneous analysis of streptavidin. This detection limit represents the ability of the method to detect as few as 20 molecules in 1 μL.

Analysis of PDGF-BB by Using Aptamer as Probe

Figure 10A:
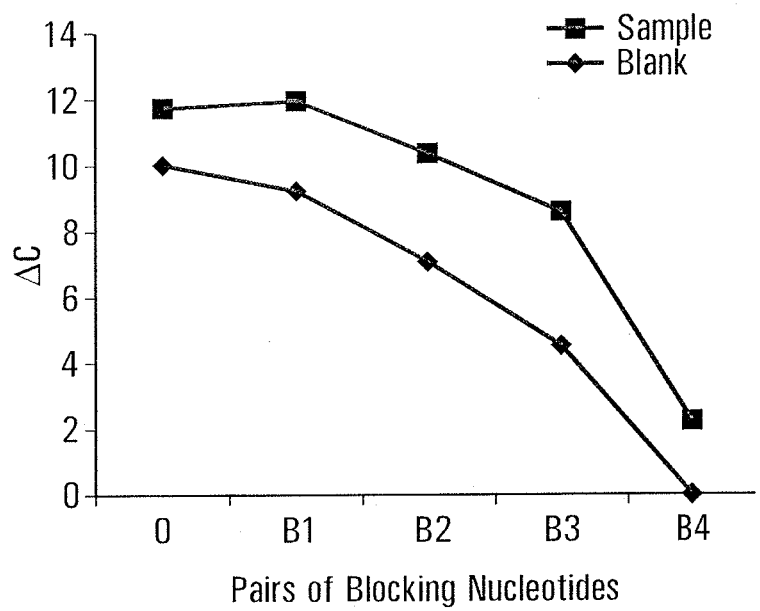
FIG. 10. Effect of the length of blocking oligonucleotides on the analysis of PDGF-BB by using probes with 6 stem bases (A) or 7 stem bases (B). In (A), B1, B2, B3, and B4 represent Block-F-1 and Block-R6-1, Block-F-2 and Block-R6-2, Block-F-3 and Block-R6-3, and Block-F-4 and Block R6-4, respectively. In (B), B1, B2, B3, and B4 represent Block-F-1 and Block-R7-1, Block-F-2 and Block R7-2, Block-F-3 and Block-R7-3, and Block-F-4 and Block R7-4, respectively. 0 means no blocking oligonucleotide was used. Sequences of the blocking oligonucleotides are shown in Table 1.
Figure 10B:
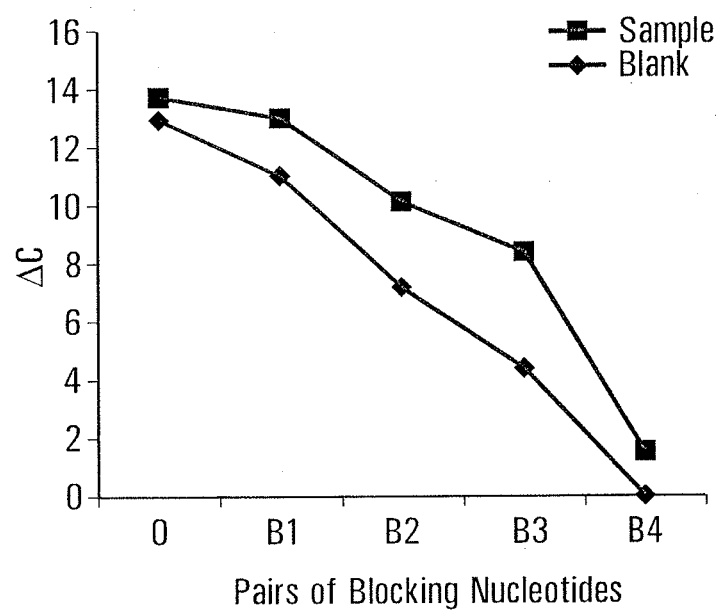
Figure 11:
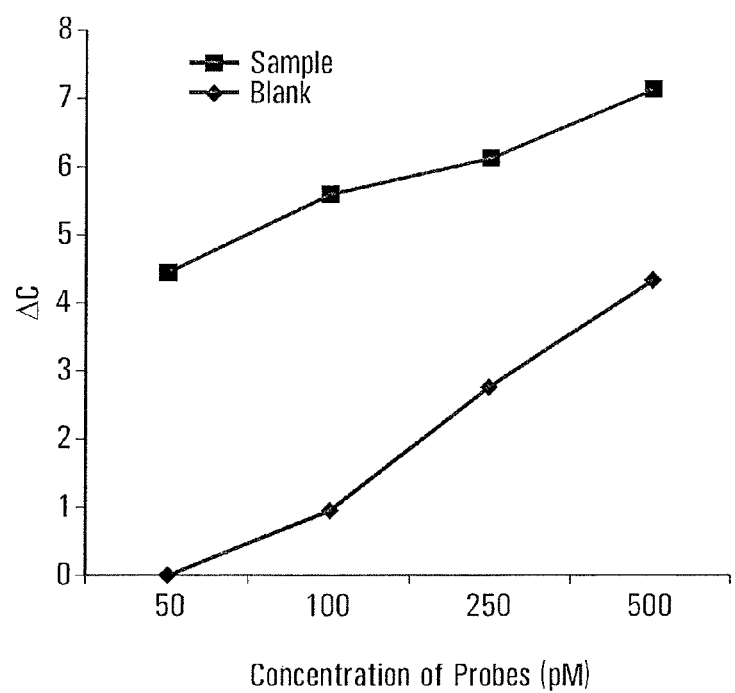
FIG. 11. Effect of the probe concentration on analysis of PDGF-BB.

Building on the success of the detection of streptavidin with extreme sensitivity, the principle was expanded to analysis of PDGF-BB by using aptamers as affinity ligands. Aptamers are short oligonucleotides that are capable of recognizing various molecular targets with high affinity and specificity (11, 12). A pair of probes was prepared by linking the above probe for streptavidin analysis with the biotinylated aptamer using the streptavidin as the intermediate molecule. Since the conjugated oligonucleotides were the same as those in the analysis of streptavidin, the focus was directed to the performance of probes with six or seven stem bases in the presence of various pairs of blocking oligonucleotides. The results are shown in FIG. 10. The impact of blocking oligonucleotides led to similar trends in analysis of PDGF-BB by using probes with six or seven stem bases. However, the probes with six stem bases provided best sensitivity when the pair of blocking oligonucleotides, Block-F3 and Block-R6-3, was used. The initial concentration of probes for analysis of PDGF-BB was optimized, and it was found that probes at 100 pM resulted in the largest $\Delta\Delta C_t$ (FIG. 11).

Figure 12A:
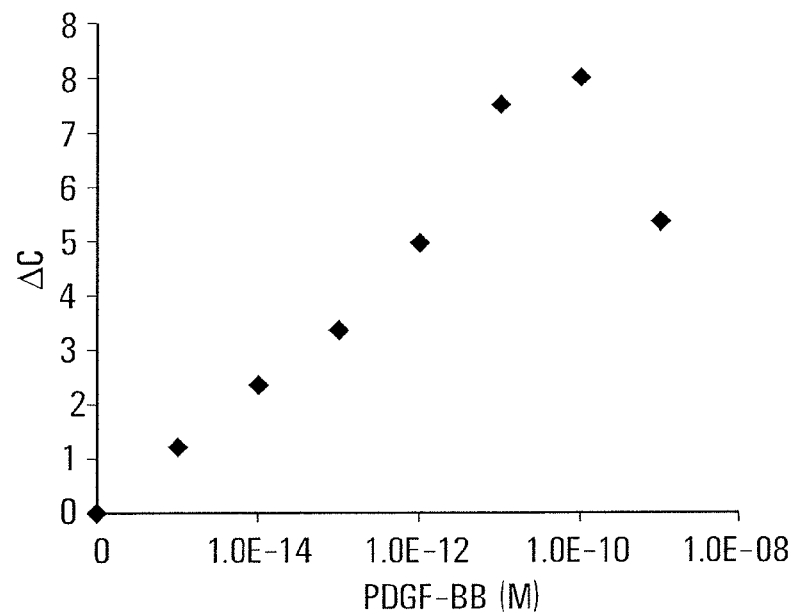
FIG. 12. Analysis of PDGF-BB in 1×PBS (A) and cell lysate (B) by binding-induced hairpin formation.
Figure 12B:
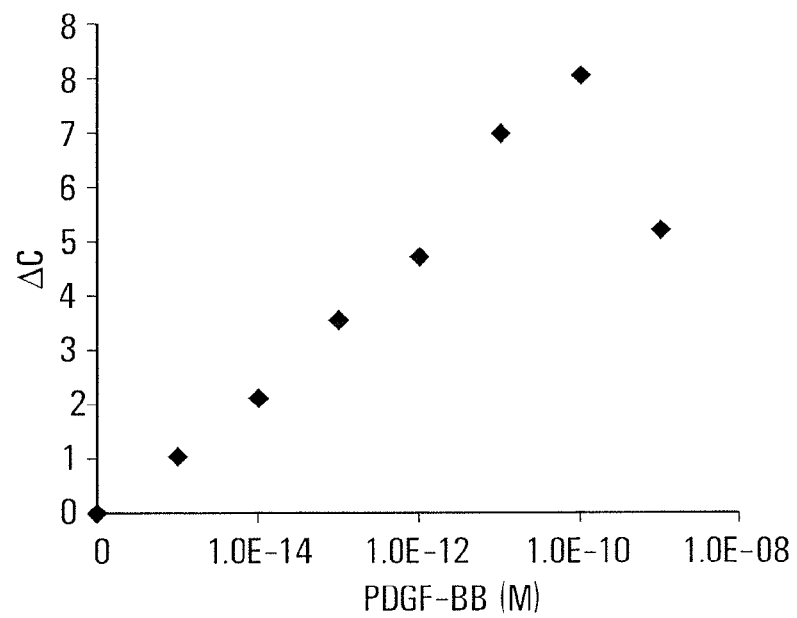

The method was demonstrated to be able to detect $5\times 10^{-16}$M PDGF-BB. A linear dynamic range of over 4 orders of magnitude ($1\times10^{-15}$ M to $1\times10^{-11}$M) was achieved (FIG. 12A). To demonstrate the applicability of the method for biological samples, the PDGF-BB spiked into mammalian cell lysate was analyzed. A similar calibration curve was obtained compared to results from the analysis of PDGF-BB in incubation buffer (FIG. 12B).

While PDGF-BB was detected with high sensitivity, other PDGF isomers AA and AB could not be detected because the aptamer binds to the B chain of PDGF with high affinity, but not to the A chain of PDGF (13).

Analysis of PSA

Figure 13A:
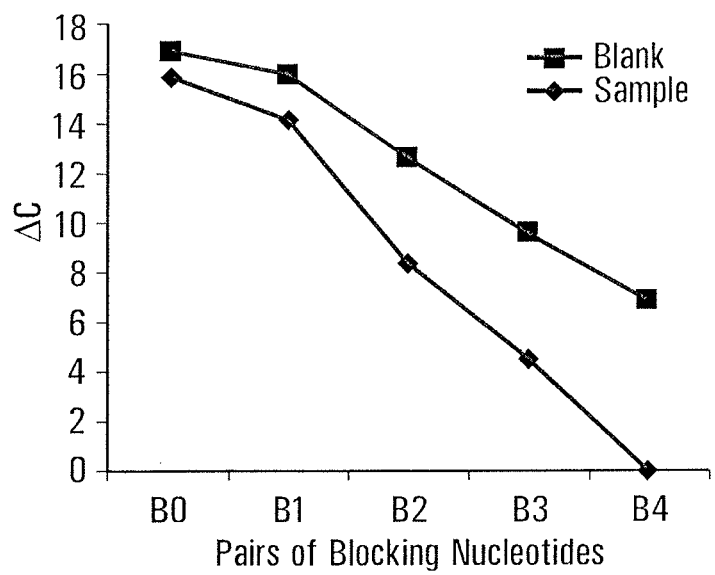
FIG. 13. Effect of the length of blocking oligonucleotides on the analysis of PSA by using probes with 6 stem bases (A) or 7 stem bases (B). In (A), B1, B2, B3, and B4 represent Block-F-1 and Block-R6-1, Block-F-2 and Block-R6-2, Block-F-3 and Block-R6-3, and Block-F-4 and Block-R6-4, respectively. In (B), B1, B2, B3, B4, and B5 represent Block-F-1 and Block-R7-1, Block-F-2 and Block-R7-2, Block-F-3 and Block-R7-3, Block-F-4 and Block-R7-4, and Block-F5 and Block-R7-4, respectively. 0 means no blocking oligonucleotide was used. Sequences of the blocking oligonucleotides are shown in Table 1.
Figure 13B:
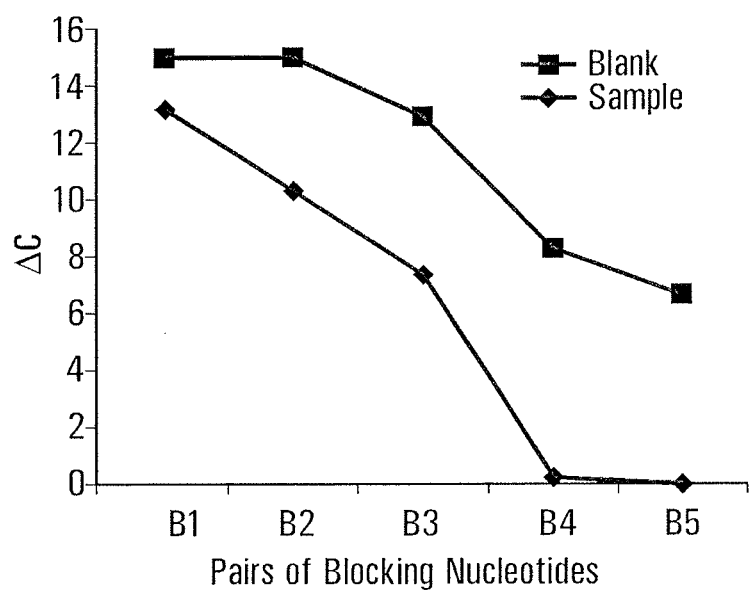
Figure 14A:
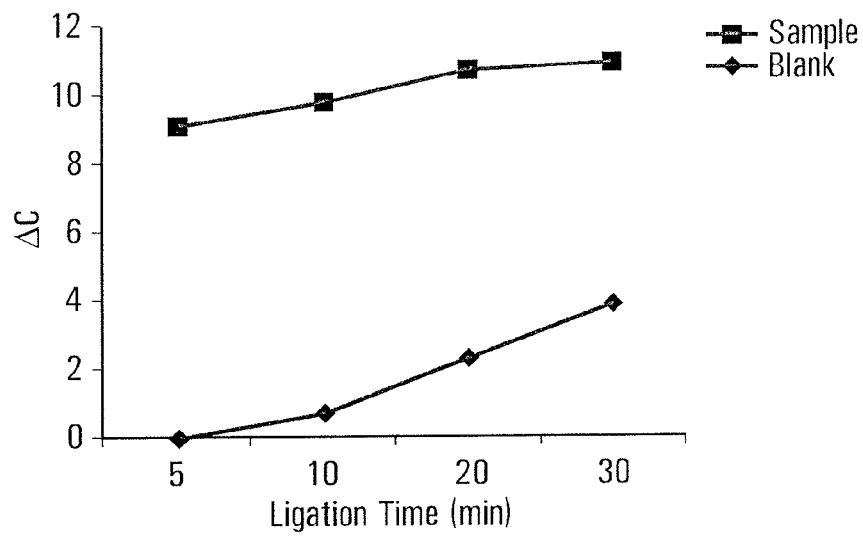
FIG. 14. Effect of the ligation time (A) and probe concentration (B) on the analysis of PSA.
Figure 14B:
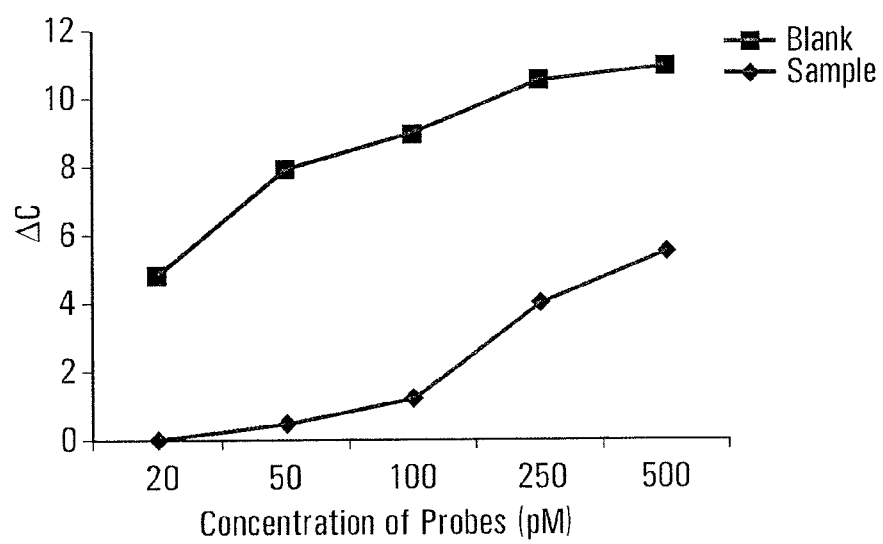

Antibodies are also able to serve as affinity ligands in the binding-induced hairpin ligation assay. To prepare the antibody-based probes for analysis of PSA, streptavidin probes were attached to biotinylated antibodies by using streptavidin as a connector. The performance of probes with six or seven stem bases was also studied in the presence of various pairs of blocking oligonucleotides. While probes with six stem bases produced the best sensitivity for detection of both streptavidin and PDGF-BB, the probes with seven stem bases led to the better results in analysis of PSA (FIG. 13). These results suggested that larger loop induced in analysis of PSA required a longer stem sequence to efficiently form the hairpin structure. Similarly, the concentration of probes and ligation time were optimized to obtain the best sensitivity (FIG. 14).

Figure 15A:
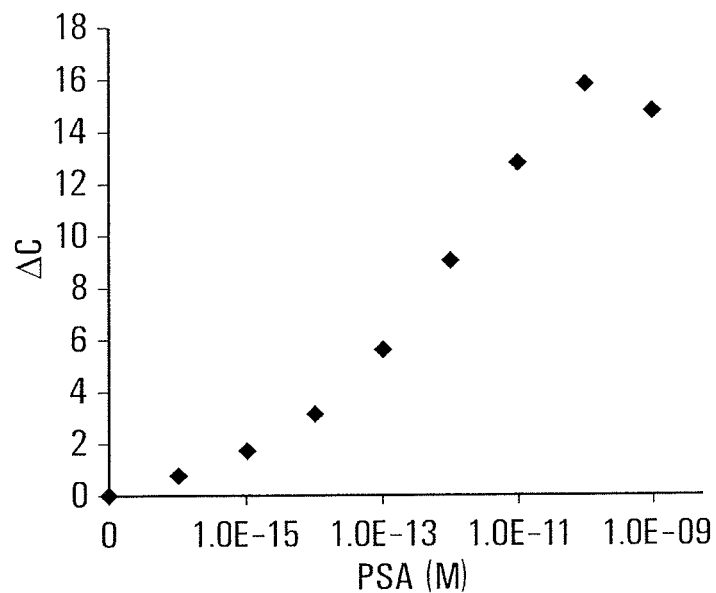
FIG. 15. Analysis of PSA in 1×PBS (A) and goat serum (B) by binding-induced hairpin assay.
Figure 15B:
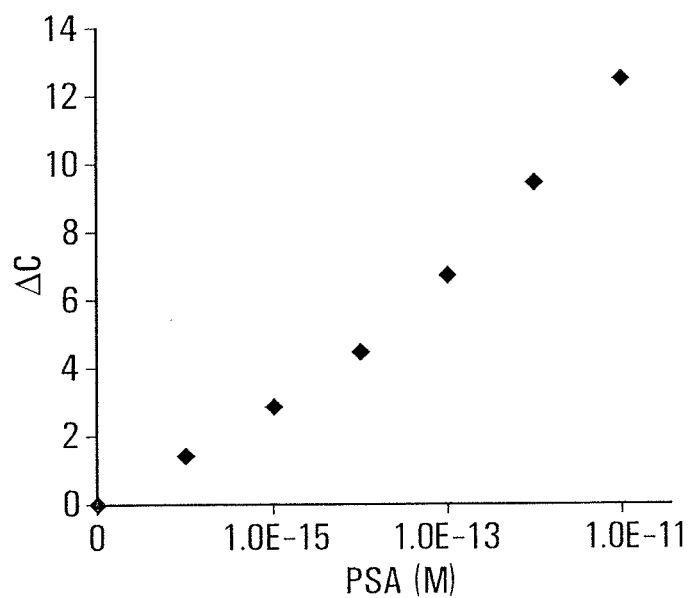

$1\times10^{-16}$ M PSA were detected, which represents the ability of the method to detect as low as 60 PSA molecules in 1 μL. A linear dynamic range of over 5 orders of magnitude ($1\times 10^{-15}$M to $1\times10^{-10}$M) was obtained (FIG. 15A). When the method was applied to detect the spiked PSA in diluted goat serum, similar sensitivity and dynamic range were achieved (FIG. 15B).

DISCUSSION AND CONCLUSIONS

The results have demonstrated a new strategy to construct a hairpin structure as a result of molecular binding. Hairpin structures could be formed once complementary sequences are present in a single nucleotide molecule. In addition to the presence of complementary sequences, the binding-induced hairpin structures resulted in the integration of separate probes with the target molecule into a single complex molecule. Therefore, the formation of binding-induced hairpin structures enables the analysis of target molecules in homogeneous solution. The adaptation of the DNA ligation technique converted the formation of hairpin structures into the synthesis of a new oligonucleotide, which allowed us to detect the target molecule using the technique for nucleic acid detection, real-time PCR. The method possesses similar potential sensitivity to the detection of nucleic acids. Three types of target molecules were detected with a sensitivity of about $10^3$- to $10^5$-fold higher than the general pM detection limit of ELISA. The sensitivity of the method is comparable to another ligation assay involving real-time PCR (14, 15). Because the occurrence of binding-induced hairpin structures also requires the two probes to bind to a single target molecule simultaneously, the method has similar specificity to other sandwich format assays. The applicability of the method was demonstrated by analysis of target molecules in cell lysate or serum.

REFERENCES

1. G. Varani, *Annu. Rev. Biophys. Biomol. Struct.*, 1995, 24, 379-404.
2. C. E. Pearson and R. R. Sinden, *Curr. Opin. Struct. Biol.*, 1998, 8, 321-330.
3. G. Bonnet, O. Krichevsky and A. Libchaber, *Proc. Natl. Acad. Sci. USA.*, 1998, 95, 8602-8606.
4. G. Bonnet, S. Tyagi, A. Libchaber and F. R. Kramer, *Proc. Natl. Acad. Sci. USA.*, 1999, 96, 6171-6176.
5. S. Tyagi and F. R. Kramer, *Nat. Biotechnol.*, 1996 14, 303-308.
6. S. Tyagi, D. P. Bratu and F. R. Kramer, *Nat. Biotechnol.*, 1998, 16, 49-53.
7. S. Tyagi, S. A. E. Marras and F. R. Kramer, *Nat. Biotechnol.*, 2000, 18, 1191-1196.
8. D. L. Sokol, X. Zhang, P. Lu and A. M. Gewirtz, *Proc. Natl. Acad. Sci. USA.*, 1998 95, 11538-11543.
9. D. Whitcombe, J. Theaker, S. P. Guy, T. Brown and S. Little, *Nat. Biotechnol.*, 1999, 17, 804-807.

10. L. Diatchenko, Y. F. Lau, A. P. Campbell, A. Chenchik, F. Moqadam, B. Huang, S. Lukyanov, K. Lukyanov, N. Gurskaya, E. D. Sverdlov and P. D. Siebert, *Proc. Natl. Acad. Sci. USA*. 1996, 93, 6025-6030.
11. A. D. Ellington and J. W. Szostak, *Nature,* 1990, 346, 818-822.
12. C. Tuerk and L. Gold, *Science,* 1990, 249, 505-510.
13. L. S. Green, D. Jellinek, R. Jenison, A. Ostman, C. H. Heldin and N. Janjic, *Biochemistry,* 1996, 35, 14413-14424.
14. S. Fredriksson, M. Gullberg, J. Jarvius, C. Ollson, K. Pietras, S. M. Gustafsdottir, A. Ostman and U. Landegren, *Nat. Biotechnol.,* 2002, 20, 473-477.
15. E. Schallmeiner, E. Oksanen, O. Ericsson, L. Spangberg, S. Eriksson, U. Stenman, K. Pettersson, U. Landegren, *Nat. Methods,* 2007, 4, 135-137.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

As used in this specification and the appended claims, the singular forms "a," "an," and "the" include plural reference unless the context clearly dictates otherwise. Unless defined otherwise all technical and scientific terms used herein have the same meaning as commonly understood to one of ordinary skill in the art to which this invention belongs.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

The invention claimed is:

1. A binding-induced hairpin detection system comprising:
   a. a first probe comprising a targeting molecule and an oligonucleotide that has a free end comprising a hairpin loop and a hairpin stem and an end attached to the targeting molecule; and
   b. a second probe comprising a targeting molecule and an oligonucleotide that has an end attached to the targeting molecule and a free end comprising a nucleotide sequence that is complementary to a nucleotide sequence at or near the free end of the oligonucleotide of the first probe;
   wherein the targeting molecule of the first and second probe is independently selected from a peptide aptamer, a protein receptor molecule, an antibody, or a ligand that is a peptide, a hormone, a lipid, or a glycan; and
   wherein upon binding of the targeting molecule to a target molecule, the free end of the oligonucleotide of the second probe hybridizes at or near the free end of the oligonucleotide of the first probe forming, a hairpin stem, the non-hybridized portions of the first and second probes together with the target molecule bound thereto forming a hairpin loop, thereby providing a binding-induced hairpin with a closed circular structure.

2. The detection system according to claim 1, wherein nucleotides at or near the free end of the oligonucleotide of the first probe and nucleotides at the free end of the oligonucleotide of the second probe comprise five to eight contiguous complementary nucleotides.

3. The detection system according to claim 1, wherein the targeting molecule is attached to the oligonucleotide via a linker.

4. The detection system according to claim 1, wherein the targeting molecule of the first probe and the targeting molecule of the second probe have distinct target specificities.

5. A method of detecting a target molecule in a sample, the method comprising:
   a. providing the sample;
   b. incubating the sample with
      i. a first probe comprising a targeting molecule and an oligonucleotide that has a free end comprising a hairpin loop and a hairpin stem and an end attached to the targeting molecule; and
      ii. a second probe comprising a targeting molecule and an oligonucleotide that has an end attached to the targeting molecule and a free end comprising a nucleotide sequence that is complementary to a nucleotide sequence at or near the free end of the oligonucleotide of the first probe;
   wherein the targeting molecule of the first and second probe is independently selected from a peptide aptamer, a protein receptor molecule, an antibody, or a ligand that is a peptide, a hormone, a lipid, or a glycan;
   c. contacting the sample with the first probe and the second probe, wherein upon binding of the targeting molecule to a target molecule, the free end of the oligonucleotide of the second probe hybridizes at or near the free end of the oligonucleotide of the first probe forming a hairpin stem, the non-hybridized portions of the first and second probes together with the target molecule bound thereto forming a hairpin loop, thereby providing a binding-induced hairpin with a closed circular structure; and
   d. detecting the binding-induced hairpin.

6. The method according to claim 5, further comprising incubating the sample with a ligase.

7. The method according to claim 6, wherein the binding-induced hairpin is detected by PCR amplification.

8. The method according to claim 5, further comprising incubating the sample with at least one blocking agent.

9. The method according to claim 5, wherein the targeting molecule is attached to the oligonucleotide via a linker.

10. The method according to claim 5, wherein the targeting molecule of the first probe and the targeting molecule of the second probe bind to the same target molecule or to two separate but associated target molecules.

11. The method according to claim 5, wherein the target molecule is an enzyme, a toxin, a cell receptor, a ligand, a viral or bacterial protein or antigen, a signal transducing agent, a cytokine, an antibody, a growth factor or a disease associated protein or antigen.

12. A binding-induced hairpin detection system comprising:
   a. a first probe comprising a targeting molecule and an oligonucleotide that has a free end comprising a hairpin loop and a hairpin stem and an end attached indirectly to the targeting molecule via a linker; and
   b. a second probe comprising a targeting molecule and an oligonucleotide that has an end attached indirectly to the targeting molecule via a linker, and a free end comprising a nucleotide sequence that is complementary to a nucleotide sequence at or near the free end of the oligonucleotide of the first probe;
   wherein the targeting molecule of the first and second probe is independently selected from an aptamer, a receptor, an antibody, or a ligand that is a peptide, a hormone, a lipid, or a glycan;

wherein the linker of the first and second probe is independently selected from a peptide linker or a binding pair, said binding pair comprising a first member attached to the probe and a second member attached to the targeting molecule; and wherein upon binding of the targeting molecule to a target molecule, the free end of the oligonucleotide of the second probe hybridizes at or near the free end of the oligonucleotide of the first probe forming a hairpin stem, the non-hybridized portions of the first and second probes together with the target molecule bound thereto forming a hairpin loop, thereby providing a binding-induced hairpin with a closed circular structure.

13. The detection system according to claim 12, wherein the first or second member of the binding pair is biotin and the other of the first or second member of the binding pair is streptavidin.

14. The detection system according to claim 12, wherein nucleotides at or near the free end of the oligonucleotide of the first probe and nucleotides at the free end of the oligonucleotide of the second probe comprise five to eight contiguous complementary nucleotides.

15. The detection system according to claim 12, wherein the targeting molecule of the first probe and the targeting molecule of the second probe have distinct target specificities.

* * * * *